United States Patent
Overmyer et al.

(10) Patent No.: US 10,588,704 B2
(45) Date of Patent: Mar. 17, 2020

(54) SURGICAL TOOL AND ROBOTIC SURGICAL SYSTEM INTERFACES

(71) Applicant: Ethicon Endo-Surgery, LLC, Guaynabo, PR (US)

(72) Inventors: Mark D. Overmyer, Cincinnati, OH (US); Jeffrey S. Swayze, West Chester, OH (US); Frederick E. Shelton, IV, Hillsboro, OH (US); Jason L. Harris, Lebanon, OH (US); Joshua Young, Loveland, OH (US); David C. Yates, West Chester, OH (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 464 days.

(21) Appl. No.: 15/374,177

(22) Filed: Dec. 9, 2016

(65) Prior Publication Data

US 2018/0161111 A1    Jun. 14, 2018

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/73* (2016.02); *A61B 46/10* (2016.02); *A61B 2017/0046* (2013.01); *A61B 2017/00398* (2013.01); *A61B 2017/00477* (2013.01); *A61B 2017/00734* (2013.01); *A61B 2017/00876* (2013.01); *A61B 2034/305* (2016.02); *A61B 2090/0813* (2016.02)

(58) Field of Classification Search
CPC ......... A61B 34/30; A61B 34/73; A61B 46/10; A61B 2034/305; A61B 2017/00477
See application file for complete search history.

(56) References Cited

U.S. PATENT DOCUMENTS

| 6,246,200 B1 | 6/2001 | Blumenkranz et al. |
| 6,331,181 B1 | 12/2001 | Tierney et al. |

(Continued)

FOREIGN PATENT DOCUMENTS

| WO | WO-2014151621 A1 | 9/2014 |
| WO | WO-2014151952 A1 | 9/2014 |
| WO | WO-2016057225 A1 | 4/2016 |

OTHER PUBLICATIONS

International Search Report and Written Opinion for PCT/US17/62153 dated Feb. 5, 2018 (8 pages).

(Continued)

*Primary Examiner* — Zakaria Elahmadi
(74) *Attorney, Agent, or Firm* — Mintz Levin Cohn Ferris Glovsky and Popeo, P.C.

(57) ABSTRACT

Various exemplary surgical tool and robotic surgical system interfaces are provided. In general, a sterile barrier can be positioned between a robotic surgical system and a surgical tool releasably coupled to the robotic surgical system. The surgical tool can be in a sterile environment on one side of the sterile barrier, and the robotic surgical system can be in a non-sterile environment on the other, opposite side of the sterile barrier. The robotic surgical system can be configured to control movement of the surgical tool releasably coupled thereto using a magnetic field that extends across the sterile barrier between the surgical tool and the robotic surgical system.

18 Claims, 15 Drawing Sheets

(51) Int. Cl.
*A61B 46/10* (2016.01)
*A61B 17/00* (2006.01)
*A61B 90/00* (2016.01)

(56) References Cited

U.S. PATENT DOCUMENTS

| | | | |
|---|---|---|---|
| 7,190,513 B2 | 3/2007 | Obrebski et al. | |
| 7,331,967 B2 | 2/2008 | Lee et al. | |
| 8,114,345 B2 | 2/2012 | Dlugos, Jr. et al. | |
| 8,398,541 B2 | 3/2013 | DiMaio et al. | |
| 8,672,922 B2 | 3/2014 | Loh et al. | |
| 8,931,682 B2* | 1/2015 | Timm | A61B 17/072 227/178.1 |
| 9,215,968 B2 | 12/2015 | Schostek et al. | |
| 9,216,061 B2* | 12/2015 | Mohr | A61B 18/24 |
| 10,149,727 B2 | 12/2018 | Overmyer et al. | |
| 10,149,732 B2 | 12/2018 | Overmyer et al. | |
| 2010/0249759 A1* | 9/2010 | Hinman | A61B 1/008 606/1 |
| 2011/0230875 A1 | 9/2011 | Walberg et al. | |
| 2012/0101495 A1* | 4/2012 | Young | A61B 17/29 606/41 |
| 2013/0041371 A1* | 2/2013 | Yates | A61B 17/07207 606/45 |
| 2013/0144306 A1* | 6/2013 | Stefanchik | A61B 17/29 606/130 |
| 2014/0005718 A1* | 1/2014 | Shelton, IV | A61B 17/07207 606/205 |
| 2015/0105798 A1* | 4/2015 | Lohmeier | A61B 34/71 606/130 |
| 2015/0164313 A1 | 6/2015 | Ouyang et al. | |
| 2015/0257842 A1* | 9/2015 | Dachs, II | A61B 90/361 606/130 |
| 2016/0270809 A1 | 9/2016 | Boudreaux et al. | |
| 2018/0161109 A1 | 6/2018 | Overmyer et al. | |
| 2018/0161110 A1 | 6/2018 | Overmyer et al. | |
| 2018/0161118 A1 | 6/2018 | Overmyer et al. | |

OTHER PUBLICATIONS

U.S. Appl. No. 15/374,145, filed Dec. 9, 2016, Surgical Tool and Robotic Surgical System Interfaces.
U.S. Appl. No. 15/374,156, filed Dec. 9, 2016, Surgical Tool and Robotic Surgical System Interfaces.
U.S. Appl. No. 15/374,108, filed Dec. 9, 2016, Surgical Tool and Robotic Surgical System Interfaces.
U.S. Appl. No. 15/200,283 entitled "Methods, Systems, and Devices for Initializing a Surgical Tool" filed Jul. 1, 2016.
U.S. Appl. No. 15/237,648 entitled "Methods, Systems, and Devices for Causing End Effector Motion With a Robotic Surgical System" filed Aug. 16, 2016.
U.S. Appl. No. 15/237,653 entitled "Methods, Systems, and Devices for Controlling a Motor of a Robotic Surgical Systems" filed Aug. 16, 2016.

* cited by examiner

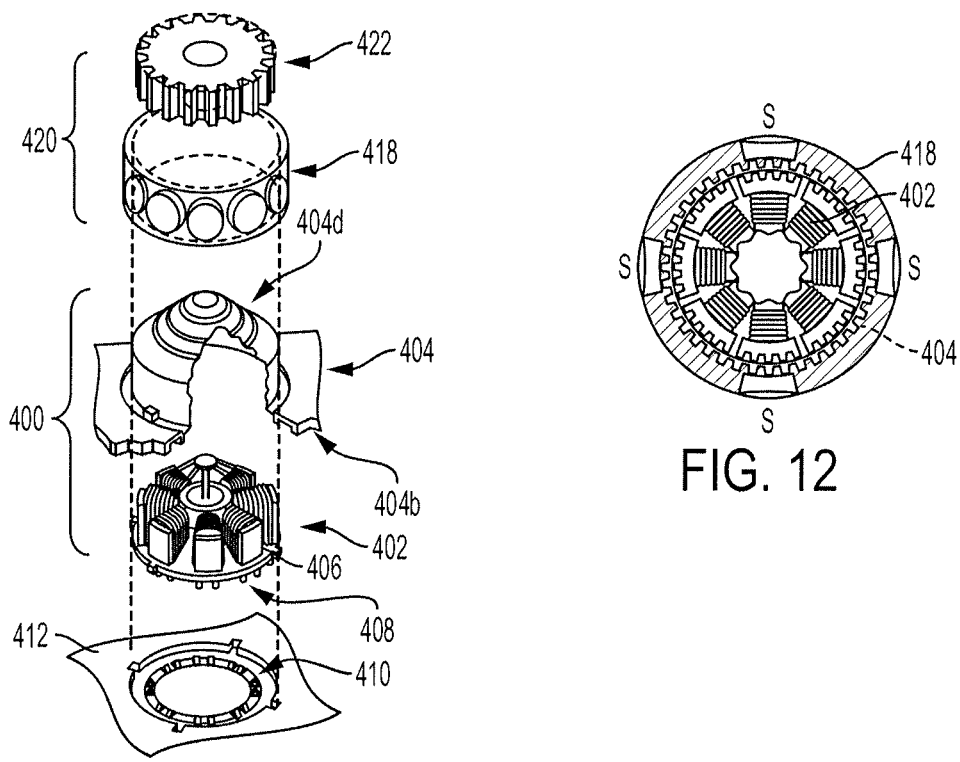
FIG. 11
FIG. 12
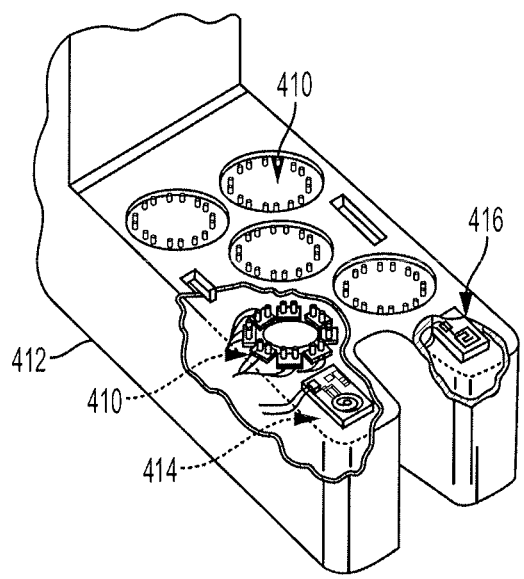
FIG. 13

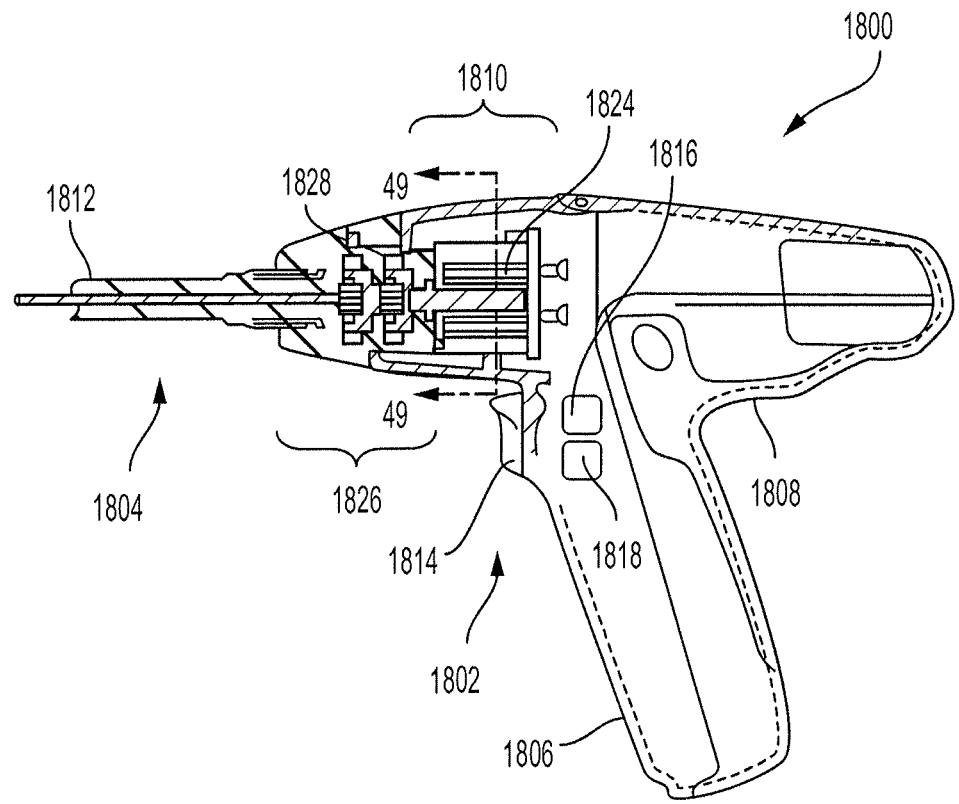
FIG. 48
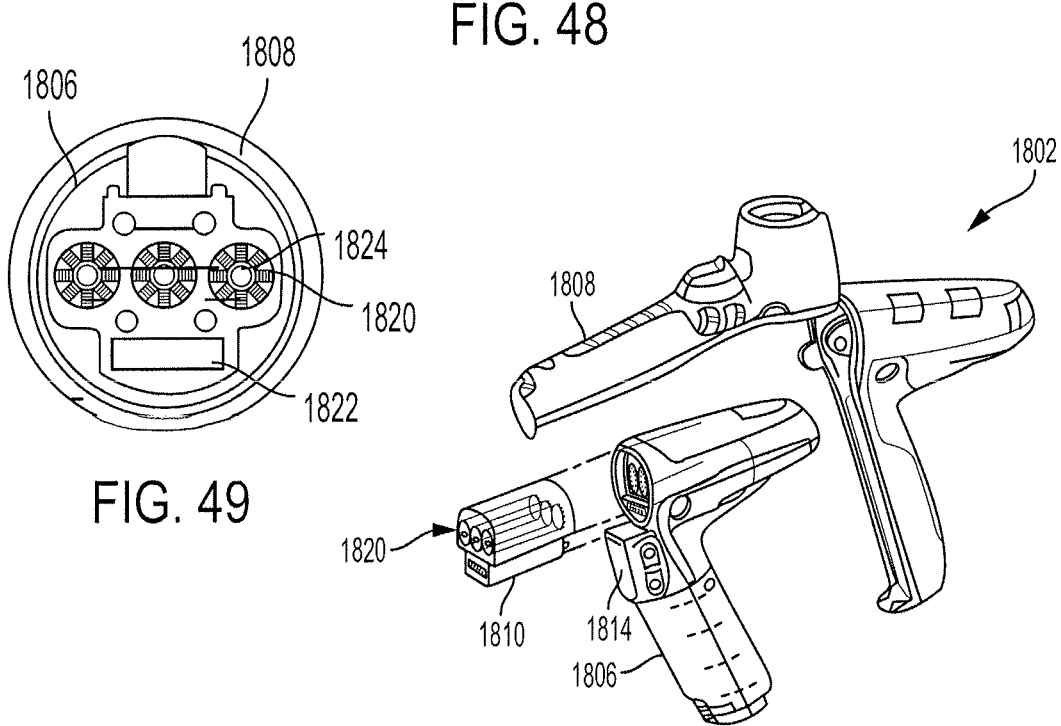
FIG. 49
FIG. 50

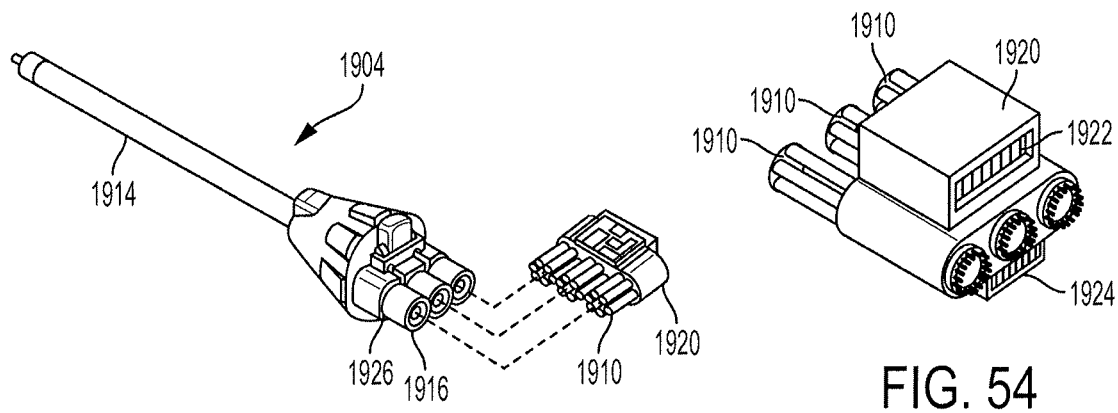
FIG. 53
FIG. 54
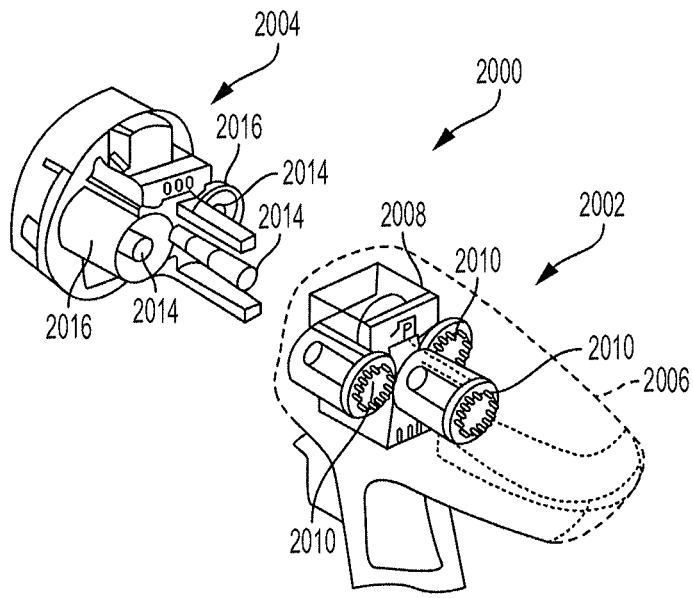
FIG. 55
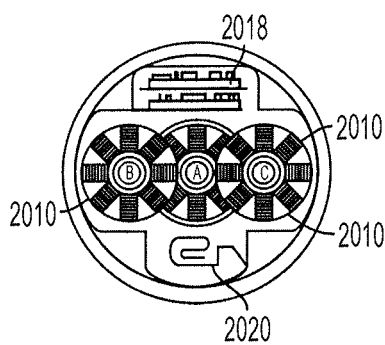
FIG. 56
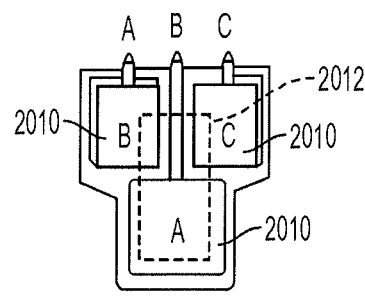
FIG. 57

SURGICAL TOOL AND ROBOTIC SURGICAL SYSTEM INTERFACES

FIELD

Methods, systems, and devices are provided for robotic surgery, and in particular surgical tool and robotic surgical system interfaces.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, surgical tool and robotic surgical system interfaces are provided.

In one aspect, a surgical system is provided that in one embodiment includes a surgical tool configured to releasably couple to a robotic surgical system with a sterile barrier being located between the surgical tool and the robotic surgical system. The surgical tool includes an elongate shaft having an end effector at a distal end thereof. The end effector is configured to move in response to generation of a magnetic field extending between a non-sterile environment proximal to the surgical tool and a sterile environment in which the surgical tool is located.

The surgical system can vary in any number of ways. For example, the surgical tool can include a rotor, and the generated magnetic field can be configured to extend between the rotor and a stator included in one of the sterile barrier and the robotic surgical system. In at least some embodiments, the surgical system can include the sterile barrier, which can include the stator. In at least some embodiments, the surgical system can include a tool driver of the robotic surgical system, and the tool driver can include the stator.

For another example, the end effector can be configured to move in response to generation of the magnetic field without the surgical tool being mechanically driven by the robotic surgical system. For yet another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

In another embodiment, a surgical system is provided that includes a sterile barrier, a surgical tool having an elongate shaft with an end effector at a distal end thereof, the surgical tool including a rotor, a robotic surgical system tool driver configured to releasably couple to the surgical tool such that the surgical tool is in a sterile environment on a first side of the sterile barrier and the tool driver is in a non-sterile environment on a second, opposite side of the sterile barrier, and a stator configured to be operatively coupled to the rotor when the tool driver is releasably coupled to the surgical tool, a magnetic field generated between the rotor and the stator being configured to cause movement of the end effector.

The surgical system can have any of a number of variations. For example, the stator can be integral with the sterile barrier. For another example, the tool driver can include the stator. For yet another example, the rotor can include a plurality of permanent magnets, and the stator can include a plurality of electromagnets. For still another example, the magnetic field can cause the end effector to move without the surgical tool being mechanically driven by the tool driver. For another example, the surgical system can include a controller configured to cause movement of the stator in response to a user input, and the movement of the stator can cause the generation of the magnetic field. For still another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

In another embodiment, a surgical system includes a surgical tool having an elongate shaft with an end effector at a distal end thereof. The surgical tool includes a rotor. The surgical system also includes a robotic surgical system tool driver configured to be electrically coupled to the surgical tool to drive a function of the end effector, and a sterile barrier located between the tool driver and the surgical tool and being configured to mechanically align the tool driver and the surgical tool.

The surgical system can have any number of variations. For example, the function of the end effector can include moving the end effector, and/or the electrical coupling can include electrically coupling a rotor of the surgical tool and a stator of the tool driver with a magnetic field extending across the sterile barrier between the rotor and the stator. The magnetic field can drive the function of the end effector without the surgical tool being mechanically driven by the tool driver.

For another example, the sterile barrier can include a plurality of protrusions extending therefrom configured to provide the mechanical alignment of the tool driver and the surgical tool. In at least some embodiments, the plurality of protrusions can be configured to be worn down in response to movement of a rotor of the surgical tool relative to a stator of the tool driver.

For yet another example, the sterile barrier can include a plurality of electrical connectors configured to provide the mechanical alignment of the tool driver and the surgical tool. In at least some embodiments, the plurality of electrical connectors can be configured to provide an electrical path for transmission of data between a first antenna of the tool driver and a second antenna of the surgical tool.

For still another example, when the tool driver is electrically coupled to the surgical tool, the surgical tool can be in a sterile environment on a first side of the sterile barrier and the tool driver can be in a non-sterile environment on a second, opposite side of the sterile barrier.

In another embodiment, a surgical system includes a surgical tool having an elongate shaft with an end effector at a distal end thereof. The surgical tool includes a rotor. The surgical system also includes a robotic surgical system tool driver configured to releasably couple to the surgical tool. The tool driver includes a stator. The surgical system also includes a sterile barrier located between the tool driver and the surgical tool such that when the tool driver is releasably coupled to the surgical tool, a magnetic field is configured to extend through the sterile barrier between the rotor on a sterile side of the sterile barrier and the stator on a non-sterile side of the sterile barrier and thereby drive a function of the end effector. The surgical system also includes a shield configured to provide a magnetic shield for the magnetic field.

The surgical system can have any number of variations. For example, the shield can be a multi-part shield that is configured to be assembled by the tool driver being releasably coupled to the surgical tool. In at least some embodiments, the shield can include a first shield that is part of the surgical tool and a second shield that is part of the tool driver, and the first and second shields can be assembled to form the multi-part shield when the tool driver is releasably coupled to the surgical tool.

For another example, the rotor can include a plurality of permanent magnets, the stator can include a plurality of electromagnets, and the shield can surround the plurality of permanent magnets and the plurality of electromagnets. For yet another example, the rotor can include a plurality of rotors, the stator can include a plurality of stators each configured to operatively couple with one of the plurality of rotors to form a rotor/stator pair, and the shield can include a plurality of shields each associated with one of the operatively coupled rotor/stator pairs. For still another example, the rotor can include a plurality of rotors, the stator can include a plurality of stators each configured to operatively couple with one of the plurality of rotors to form a rotor/stator pair, and the shield can include a single shield that provides the magnetic shield for each of the rotor/stator pairs. For another example, the shield can include mu-metal. For still another example, when the tool driver is releasably coupled to the surgical tool, the rotor can be in a sterile environment on a first side of the sterile barrier and the stator can be in a non-sterile environment on a second, opposite side of the sterile barrier. For another example, the electric coupling of the rotor and the stator can drive the function of the end effector without the surgical tool being mechanically driven by the tool driver. For yet another example, the function of the end effector can include moving the end effector. For still another example, the function of the end effector can include at least one of closing the end effector, opening the end effector, articulating the end effector relative to an elongate shaft of the surgical tool that has the end effector at a distal end thereof, rotating the end effector relative to the elongate shaft, and rotating the end effector and the elongate shaft as a unit about a longitudinal axis of the elongate shaft.

In another embodiment, a surgical system includes a surgical tool having an elongate shaft with an end effector at a distal end thereof, a sterile barrier, and a robotic surgical system tool driver configured to releasably couple to the surgical tool with the sterile barrier located therebetween. The end effector is configured to move in response to generation of a magnetic field extending through the sterile barrier and between the surgical tool and the robotic surgical system. The surgical system also includes a shield configured to provide magnetic shielding of the magnetic field.

The surgical system can vary in any number of ways. For example, the shield can be a multi-part shield that is configured to be assembled by the tool driver being releasably coupled to the surgical tool. For another example, the surgical tool can include a rotor, the tool driver can include a stator, and the shield can surround the rotor and the stator. For yet another example, the generation of the magnetic field can be configured to drive the function of the end effector without the surgical tool being mechanically driven by the tool driver. For another example, the shield can include mu-metal. For yet another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

In another aspect, a surgical method is provided that in one embodiment includes coupling a surgical tool to a tool driver of a robotic surgical system with a sterile barrier between the surgical tool and the tool driver such that the surgical tool is in a sterile environment, and causing a magnetic field to extend between the surgical tool and the robotic surgical system through the sterile barrier and thereby drive a function of an end effector of the surgical tool.

The surgical method can vary in any number of ways. For example, coupling the surgical tool to the robotic surgical system can electrically couple a rotor of the surgical tool to a stator of the robotic surgical system with the sterile barrier being between the rotor and the stator such that the rotor is in the sterile environment on one side of the sterile barrier and the stator is in a non-sterile environment on another side of the sterile barrier. For another example, coupling the surgical tool to the robotic surgical system can electrically couple a rotor of the surgical tool to a stator of the sterile barrier. For yet another example, the surgical tool can be in the sterile environment on one side of the sterile barrier and the tool driver can be in a non-sterile environment on another side of the sterile barrier. For still another example, the magnetic field can drive the function of the end effector without the surgical tool being mechanically driven by the tool driver. For another example, the function of the end effector can include moving the end effector. For still another example, the function of the end effector can include at least one of closing the end effector, opening the end effector, articulating the end effector relative to an elongate shaft of the surgical tool that has the end effector at a distal end thereof, rotating the end effector relative to the elongate shaft, and rotating the end effector and the elongate shaft as a unit about a longitudinal axis of the elongate shaft.

In another embodiment, a surgical method includes coupling a surgical tool to a tool driver of a robotic surgical system with a sterile barrier being located between the surgical tool and the tool driver and including a mating feature that mechanically aligns a rotor of the surgical tool with a stator of the tool driver, and causing a magnetic field to extend between the rotor and the stator through the sterile barrier and thereby cause movement of an end effector of the surgical tool.

The surgical method can have any number of variations. For example, the mating feature can include a plurality of protrusions extending from the sterile barrier, and movement of the rotor when the magnetic field extends between the rotor and the stator can cause the plurality of protrusions to be worn down. For another example, the magnetic field can cause the movement of the end effector without the surgical tool being mechanically driven by the tool driver. For yet another example, with the surgical tool and the tool driver coupled together, the surgical tool can be in a sterile environment on one side of the sterile barrier and the tool driver can be in a non-sterile environment on another side of the sterile barrier. For still another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

In another embodiment, a surgical method is provided that includes coupling a surgical tool to a tool driver of a robotic surgical system with a sterile barrier being located between the surgical tool and the tool driver such that the surgical tool is in a sterile environment on one side of the sterile barrier and the tool driver is in a non-sterile environment on another side of the sterile barrier. The sterile barrier includes an electrical connector that mechanically aligns an antenna of the surgical tool with an antenna of the tool driver. The surgical method also includes causing data to be transmitted between the antenna of the surgical tool and the antenna of the tool driver through the electrical connector.

The surgical method can vary in any number of ways. For example, the electrical connector can extend through the sterile barrier along a tortuous path. For another example, the electrical connector can have one end thereof exposed on the one side of the sterile barrier and has another end thereof exposed on the other side of the sterile barrier. For yet another example, the data can be optically transmitted, and the sterile barrier can be transparent or semi-transparent to allow the optical transmission of the data therethrough.

In another embodiment, a surgical method includes coupling a surgical tool to a tool driver of a robotic surgical system with a sterile barrier between the surgical tool and the tool driver such that the surgical tool is in a sterile environment, and causing a magnetic field to extend between a rotor of the surgical tool and a stator of the robotic surgical system through the sterile barrier and thereby move an end effector of the surgical tool, a shield surrounding the rotor and the stator providing a magnetic shield of the magnetic field.

The surgical method can have any number of variations. For example, the shield can be a multi-part shield, and coupling the surgical tool to the tool driver can assemble the shield. For another example, the sterile barrier can include the shield as an integral part thereof.

In another embodiment, a surgical method includes coupling a distal portion of a handheld surgical device to a proximal portion of the handheld surgical device with a handle in the proximal portion being in a non-sterile environment and a sterile barrier of the handheld surgical device providing a sterile environment for the distal portion including an elongate shaft having an end effector at a distal end thereof, and causing a magnetic field to extend between the proximal portion in the non-sterile environment and the distal portion in the sterile environment and thereby move the end effector.

The surgical method can vary in any number of ways. For example, coupling the distal portion to the proximal portion can electrically couple a rotor of the distal portion to a stator of the proximal portion, and the magnetic field can extend between the stator and the rotor. For another example, the magnetic field can cause the movement of the end effector without the surgical tool being mechanically driven by the tool driver. For yet another example, the surgical method can include, prior to coupling the distal portion to the proximal portion, coupling the sterile barrier to the proximal portion. For still another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

In another aspect, a surgical device is provided that in one embodiment includes a proximal handle portion of a surgical tool including a stator, and a distal portion of the surgical tool configured to removably and replaceably couple to the proximal handle portion. The distal portion includes a rotor and includes an end effector configured to be driven by a magnetic field extending between the rotor and the stator. The surgical device also includes a sterile barrier coupled to the proximal handle portion and configured to provide a sterile environment for the distal portion when the distal portion is removably and replaceably coupled to the proximal handle portion.

The surgical device can vary in any number of ways. For example, the distal portion can be configured to removably and replaceably couple to the proximal portion by engaging the rotor with the stator. For another example, the sterile barrier can be removably and replaceably coupled to the proximal handle portion. For yet another example, the stator can be integrally coupled to the proximal handle portion. For still another example, the stator can be removably and replaceably coupled to the proximal handle portion. For another example, the magnetic field can drive the end effector to move without the surgical tool being mechanically driven by the tool driver. For still another example, the end effector can be configured to be driven to effect at least one of closing the end effector, opening the end effector, articulating the end effector relative to an elongate shaft having the end effector at a distal end thereof, rotating the end effector relative to the elongate shaft, and rotating the end effector and the elongate shaft as a unit about a longitudinal axis of the elongate shaft.

In another embodiment, a surgical device includes an elongate shaft having an end effector at a distal end thereof that is configured to engage tissue, a proximal handle configured to be handheld and to removably and replaceably couple to the elongate shaft such that the elongate shaft extends distally from the proximal handle, and a sterile barrier coupled to the proximal handle and configured to provide a sterile environment distal thereof with a non-sterile environment being proximal thereto. The elongate shaft and the end effector are in the sterile environment when the proximal handle is removably and replaceably coupled to the elongate shaft. The surgical device also includes magnetic members configured to generate a magnetic field across the sterile barrier when the proximal handle is removably and replaceably coupled to the elongate shaft and thereby cause movement of the end effector.

The surgical device can have any number of variations. For example, the magnetic members can include a rotor of the elongate shaft and a stator of the proximal handle. In at least some embodiments, the rotor can be at a proximal end of the elongate shaft, the stator can be at a distal end of the proximal handle, and the proximal handle can be configured to be removably and replaceably coupled to the elongate shaft by attaching the rotor to the stator.

For another example, the proximal handle can include a power source configured to cause the generation of the magnetic field. For yet another example, the movement of the end effector can include at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

BRIEF DESCRIPTION OF DRAWINGS

This invention will be more fully understood from the following detailed description taken in conjunction with the accompanying drawings, in which:

FIG. 11 is an exploded view of one embodiment of a sterile barrier including a stator and configured to be coupled to a tool driver and to a rotor of a surgical tool housing;

FIG. 12 is an end cross-sectional view of the sterile barrier and rotor of FIG. 11 coupled together;

FIG. 13 is a perspective, partial cut-away view of the tool driver of FIG. 11;

FIG. 48 is a side transparent view of one embodiment of a surgical device including a proximal portion and a distal portion that is releasably coupled to the proximal portion;

FIG. 49 is a cross-sectional view of the surgical device of FIG. 48;

FIG. 50 is an exploded view of the proximal portion of the surgical device of FIG. 48;

FIG. 53 is a perspective view of the distal portion and a stator of the proximal portion of the surgical device of FIG. 52;

FIG. 54 is a perspective view of the stator of FIG. 53;

FIG. 55 is a side, partially transparent view of another embodiment of a surgical device including a proximal portion that includes a stator and a distal portion that includes a rotor and is configured to releasably couple to the proximal portion;

FIG. 56 is a schematic cross-sectional view of the proximal portion of the surgical device of FIG. 55;

FIG. 57 is a top schematic view of a portion of proximal portion of the surgical device of FIG. 56;

DETAILED DESCRIPTION

Figure 1:
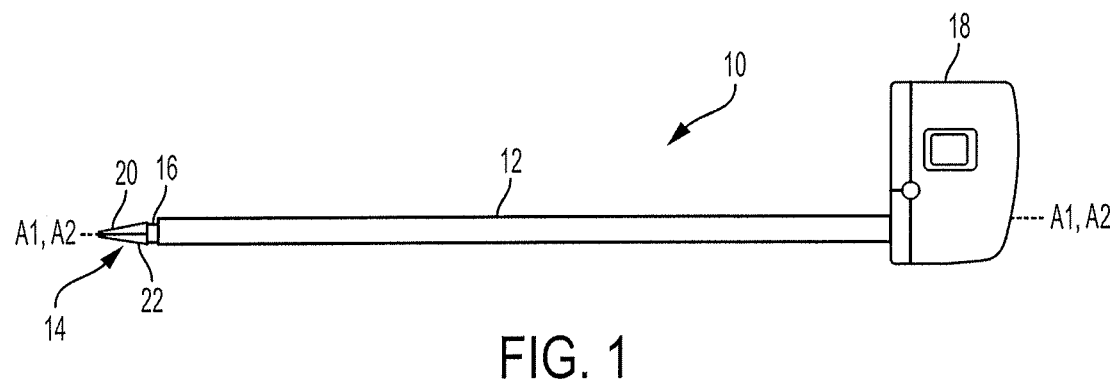
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Surgical tool and robotic surgical system interfaces are provided. In general, a sterile barrier can be positioned between a robotic surgical system (also referred to herein as a "surgical robot") and a surgical tool releasably coupled to the robotic surgical system. The surgical tool can be in a sterile environment on one side of the sterile barrier, and the surgical robot can be in a non-sterile environment on the other, opposite side of the sterile barrier. The sterile barrier may thus be configured as an interface between the surgical tool and the surgical robot at which the surgical tool releasably couples to the surgical robot. The surgical robot can be configured to control movement of the surgical tool releasably coupled thereto using a magnetic field that extends across the sterile barrier between the surgical tool and the surgical robot. The surgical robot can thus be configured to cause movement of the surgical tool electrically (e.g., via electromagnetic field) without the movement being mechanically driven by the surgical robot and without any mechanical parts extending across the sterile barrier to mechanically transfer movement from the surgical robot to the surgical tool. The sterile barrier may thus be a simple mechanical part that does not include any moving parts, which may facilitate disposability of the sterile barrier (e.g., discarding the sterile barrier after its use with one patient) and/or reduce its cost of manufacture.

In other embodiments, a sterile barrier can be positioned between a proximal portion of a surgical tool and a distal portion of the surgical tool that is releasably coupled to the surgical tool's proximal portion. The proximal portion can include the tool's handle, and the distal portion can include the tool's elongate shaft that extends distally from the handle and can include the tool's end effector at a distal end of the shaft. The shaft and end effector can be in a sterile environment on one side of the sterile barrier, and the handle can be in a non-sterile environment on the other, opposite side of the sterile barrier. The sterile barrier may thus be configured as an interface between the handle and the shaft and end effector. Components in the handle can be configured to control movement of the end effector and shaft releasably coupled to the handle using a magnetic field that extends across the sterile barrier between the tool's proximal portion and the tool's distal portion.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

Figure 2:
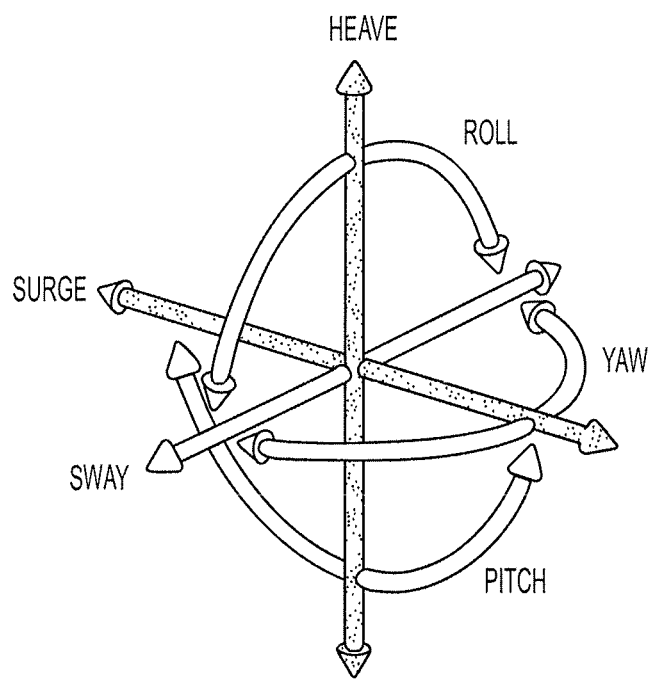
FIG. 2 is a graphical representation of terminology associated with six degrees of freedom.

The wrist 16 can have any of a variety of configurations. Exemplary embodiments of a wrist of a surgical tool and of effecting articulation at the wrist are described in International Patent Publication No. WO 2014/151952 entitled "Compact Robotic Wrist" filed on Mar. 13, 2014, International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane. FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The movement of the end effector 14 in this illustrated embodiment includes articulating movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1. The movement of the end effector 14 in this illustrated embodiment also includes rotational movement of the end effector 14 in which the end effector 14 rotates about its longitudinal axis A2, either with or without corresponding rotation of the shaft 12 about its longitudinal axis A1.

Figure 3:
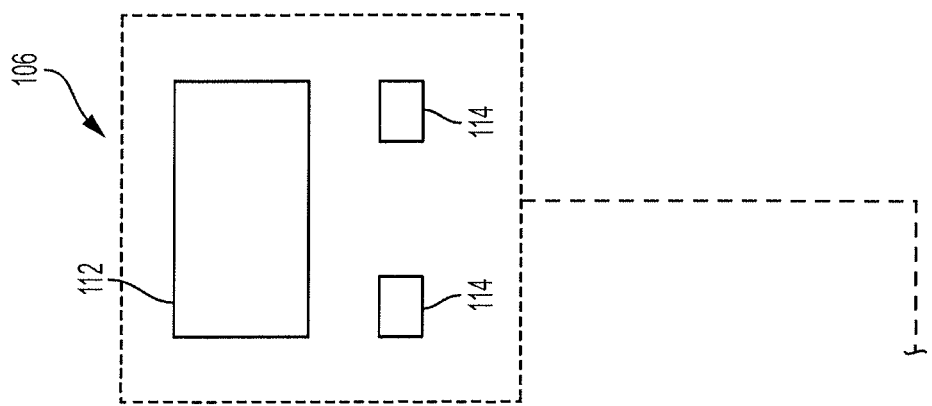
FIG. 3 is a perspective view of one embodiment of a robotic surgical system that includes a patient-side portion and a user-side portion.
Figure 3:
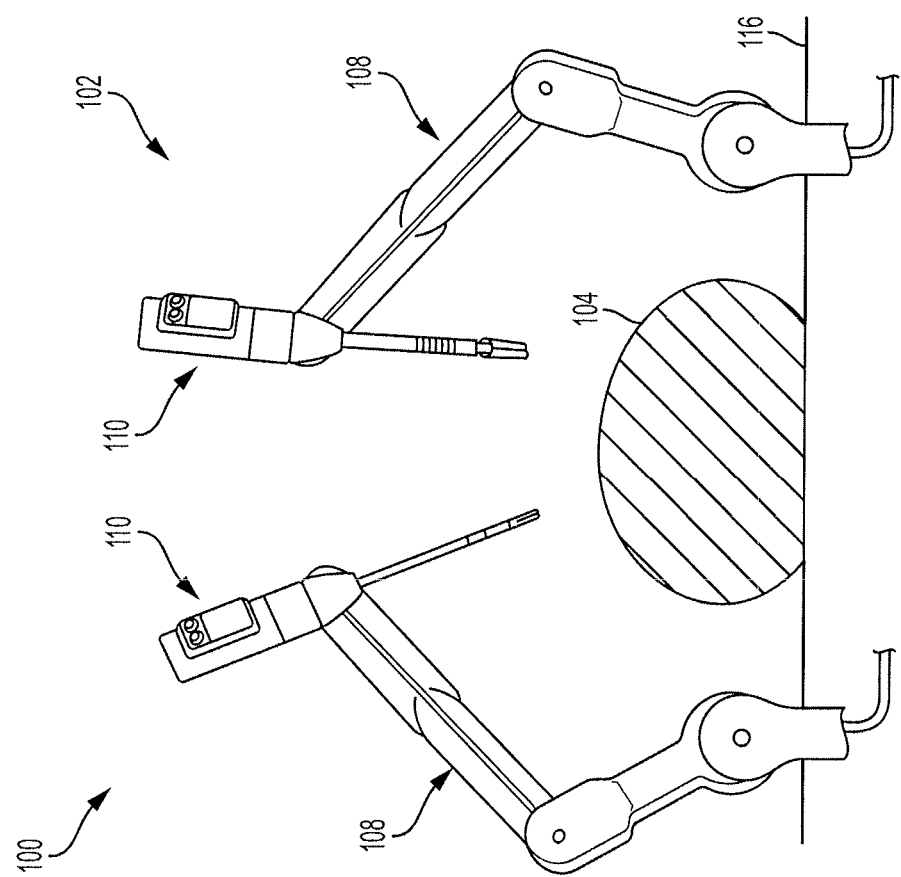

FIG. 3 is a perspective view of one embodiment of a robotic surgical system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 3, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 3). Alternatively, the patient-side portion 102 can include a single assembly that includes one or more robotic arms 108 extending therefrom.

Figure 4:
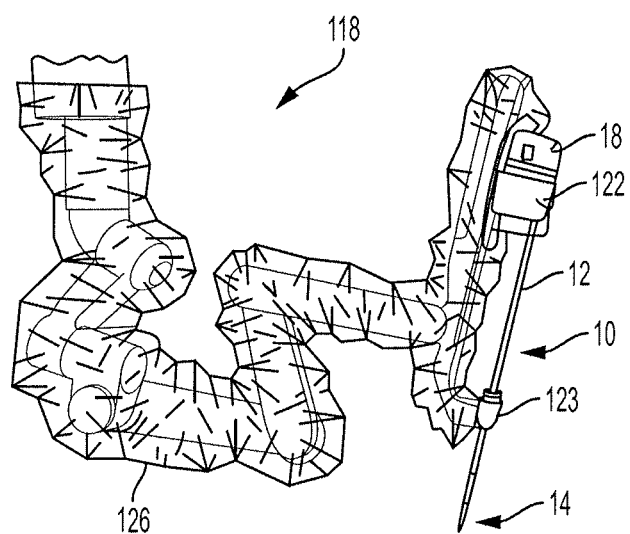
FIG. 4 is a perspective view of one embodiment of a robotic arm of a robotic surgical system with the surgical tool of FIG. 1 releasably and replaceably coupled to the robotic arm.

FIG. 4 illustrates another embodiment of a robotic arm 118 and the surgical tool 10 of FIG. 1 releasably and replaceably coupled to the robotic arm 118. Other surgical instruments can instead be coupled to the arm 118, as discussed herein. The robotic arm 118 is configured to support and move the associated tool 10 along one or more degrees of freedom (e.g., all six Cartesian degrees of freedom, five or fewer Cartesian degrees of freedom, etc.).

The robotic arm 118 can include a tool driver 122 at a distal end of the robotic arm 118, which can assist with controlling features associated with the tool 10. The robotic arm 118 can also include an entry guide 123 (e.g., a cannula mount, cannula, etc.) that can be a part of or releasably and replaceably coupled to the robotic arm 118, as shown in FIG. 4. A shaft of a tool assembly can be inserted through the entry guide 123 for insertion into a patient, as shown in FIG. 4 in which the shaft 12 of the tool 10 of FIG. 1 is shown inserted through the entry guide 123.

In order to provide a sterile operation area while using the surgical system, a barrier 126 can be placed between the actuating portion of the surgical system (e.g., the robotic arm 118) and the surgical instruments coupled thereto (e.g., the tool 10, etc.). A sterile component, such as an instrument sterile adapter (ISA), can also be placed at the connecting interface between the tool 10 and the robotic arm 118. The placement of an ISA between the tool 10 and the robotic arm 108 can ensure a sterile coupling point for the tool 10 and the robotic arm 118. This permits removal of surgical instruments from the robotic arm 118 to exchange with other surgical instruments during the course of a surgery without compromising the sterile surgical field.

Figure 5:
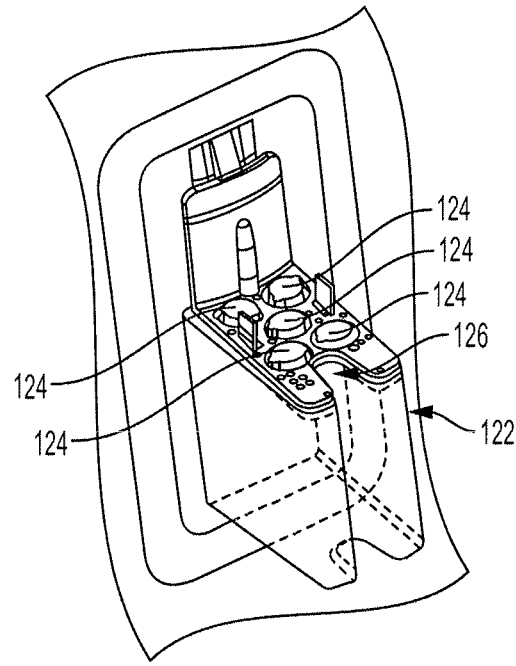
FIG. 5 is a perspective view of a tool driver of the robotic arm of FIG. 4.

FIG. 5 illustrates the tool driver 122 in more detail. As shown, the tool driver 122 includes one or more motors, e.g., five motors 124 are shown, that control a variety of movements and actions associated with the tool 10 coupled to the arm 118. For example, each motor 124 can couple to and/or interact with an activation feature (e.g., gear) associated with the tool 10 for controlling one or more actions and movements that can be performed by the tool 10, such as for assisting with performing a surgical operation. The motors 124 are accessible on the upper surface of the tool driver 122, and thus the tool 10 (e.g., the housing 18 thereof) is configured to mount on top of the tool driver 122 to couple thereto. Exemplary embodiments of motor operation and components of a tool housing (also referred to as a "puck") configured to controlled by tool driver motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

The tool driver 122 also includes a shaft-receiving channel 126 formed in a sidewall thereof for receiving the shaft 12 of the tool 10. In other embodiments, the shaft 12 can extend through on opening in the tool driver 122, or the two components can mate in various other configurations.

Figure 6:
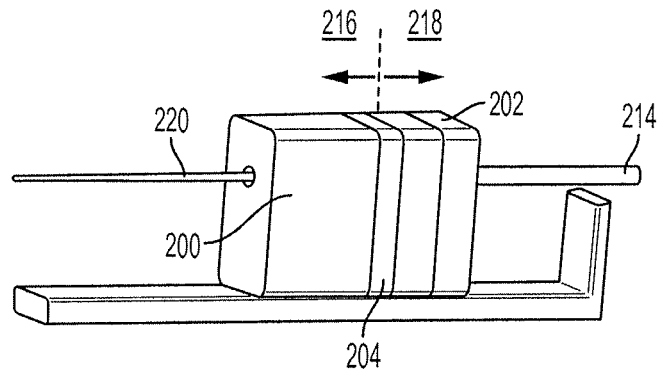
FIG. 6 is a perspective view of one embodiment of a tool driver coupled to a surgical tool housing with a sterile barrier positioned therebetween.
Figure 7:
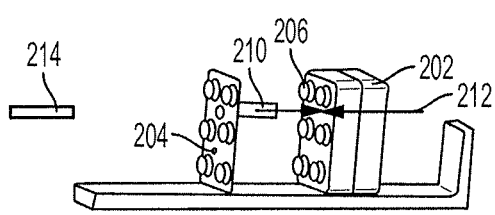
FIG. 7 is an exploded view of the tool driver, surgical tool housing, and sterile barrier of FIG. 6 prior to coupling thereof.

As mentioned above, a surgical robot can be configured to releasably couple to a surgical tool at a sterile barrier, and the surgical robot can be configured control movement of the surgical tool releasably coupled thereto using a magnetic field that extends between the surgical tool and the surgical robot. FIG. 6 illustrates one embodiment of a surgical tool housing 200 of a surgical tool (e.g., the tool 10 of FIG. 1 or another surgical tool) configured to releasably couple to a tool driver 202 of a robotic surgical system (e.g., the robotic surgical system 100 of FIG. 3 or another robotic surgical system) at a sterile barrier 204. The tool driver 202 in this illustrated embodiment has six motor stator areas 206, as shown in FIG. 7. The sterile barrier 204 thus has six motor seating areas 208 each configured seat one of the motorstator areas 206 therein, as shown in FIGS. 7 and 8.

Figure 8:
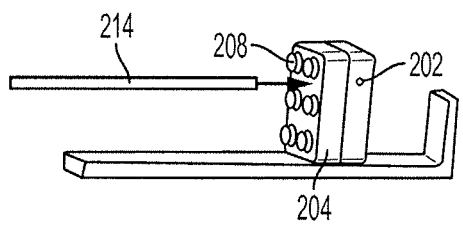
FIG. 8 is an exploded view of the tool driver and sterile barrier of FIG. 7 coupled together prior to the coupling of the surgical tool housing therewith.
Figure 9:
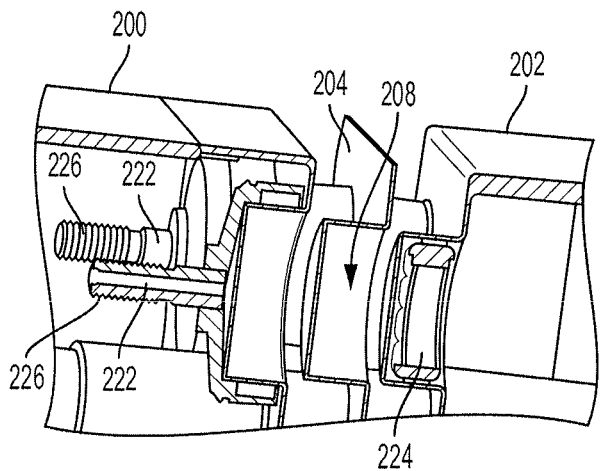
FIG. 9 is an exploded cross-sectional view of portions of the tool driver, surgical tool housing, and sterile barrier of FIG. 6 prior to complete coupling thereof.
Figure 10:
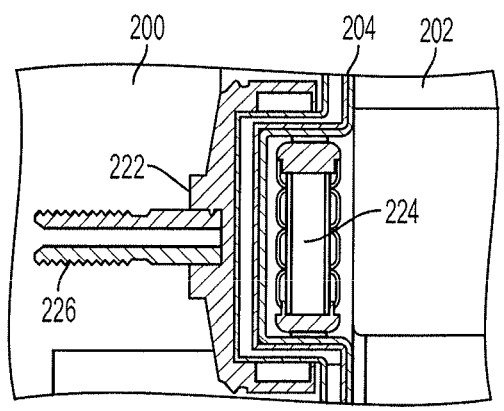
FIG. 10 is an exploded cross-sectional view of portions of the tool driver, surgical tool housing, and sterile barrier of FIG. 6.

FIGS. 6-8 also illustrate an embodiment of coupling the sterile barrier 204 to the surgical robot and coupling the surgical tool to the coupled sterile barrier 204 and surgical robot. A mating element 210 of the sterile barrier 204, which is an elongate cannulated shaft in this illustrated embodiment, can be mated to a corresponding mating feature 212 of the surgical robot 202, which is an elongate bore in this illustrated embodiment. Then, the surgical tool can be coupled to the surgical robot with the sterile barrier 204 positioned therebetween, such as by an elongate coupling shaft 214 of the surgical tool being advanced through the cannulated shaft 210 and bore 212, as shown in FIG. 9. When assembled as shown in FIGS. 6 and 10, the sterile barrier 204 defines on a first side 216 thereof a sterile environment, in which the tool housing 200 and elongate shaft 220 extending therefrom are located, and on a second, opposite side thereof a non-sterile environment, in which the tool driver 202 is located. As shown in FIG. 10, when the surgical tool is releasably coupled to the surgical robot, no mechanical parts extend therebetween through the sterile barrier 204.

As shown in FIGS. 9 and 10, the surgical tool includes a rotor 222 at the tool housing 200, and the surgical robot includes a stator 224 at the tool driver 202. Each of the motors (e.g., stepper or brushless motors) has associated therewith a stator 224 such that the tool driver 202 has six stators 224 in this illustrated embodiment. The surgical tool in this illustrated embodiment thus has six rotors 222, each configured to operatively couple to one of the stators 224. As in this illustrated embodiment, each of the stators 224 can include an electromagnet, and each of the rotors 222 can include a permanent magnet. The rotors 222 and stators 224 can have other configurations, as will be appreciated by a person skilled in the art. In other embodiments, the tool driver of the surgical robot can include the rotors, and the tool housing of the surgical tool can include the stators.

The robotic surgical system, e.g., a control system thereof, is configured to control the stators 224 to cause movement thereof such that current in the stators 224 create a magnetic field, e.g., as in a DC brushless or stepper motor. The magnetic field extends from the tool driver 202, e.g., from the stators 224, through the sterile barrier 204 to the surgical tool on the other side of the sterile barrier 204, e.g., to the rotors 222 at the tool's housing 200. The magnetic field influences the rotors 222, e.g., the permanent magnets, to impart torque thereto. The rotors 222 are directly attached to an activation feature in the form of tool drive trains, e.g., lead screws 226, cable spindles, gear boxes, etc., as shown in FIGS. 9 and 10. The drive trains are operatively coupled to the surgical tool's end effector. The torque at the rotors 222 can thus cause movement of the end effector via the drive trains. Torque can be delivered to one or more of the rotors 222 via their associated one or more of the stators 224 to cause selected one or more of the drive trains to cause a selected movement of the end effector, e.g., articulation, jaw opening, jaw closing, etc. The moving parts to impart end effector movement (and also possible elongate shaft movement) can thus all be located distal to the sterile barrier 204 since the moving rotors 222 and moving activation feature are located distal to the sterile barrier 204.

The tool driver 202 can include one or more sensors configured to facilitate position control of the rotors 222. For example, the one or more sensors can be Hall effect sensors located at each of the stator's coil or winding. A voltage measured by the Hall effect sensors will jump when the rotors 222 (e.g., the permanent magnets) move relative to the coils or windings. The robotic surgical system's control system can be configured to use this voltage to keep track of the jumps to measure incremental rotary position of the rotors 222 and control the stators 224 accordingly.

As shown in FIGS. 9 and 10, when the surgical tool is releasably coupled to the surgical robot, no mechanical parts extend therebetween through the sterile barrier 204. Accordingly, no mechanical movement is transferred from the tool driver 202 to the tool housing 200 in the surgical robot controlling the surgical tool. Instead the surgical robot can electronically control the surgical tool via electromagnetic energy. Further, the sterile barrier 204 does not include any mechanical parts that move during the surgical robot's control of the surgical tool's movement.

In the embodiment of FIGS. 6-10, the tool driver 202 includes the stator 224 that is operatively coupled to the rotor 222 of the surgical tool releasably coupled to the surgical robot. In other embodiments, a sterile barrier between a tool driver and a surgical tool releasably coupled thereto can include a stator as an integral part thereof, with the surgical tool including the rotor configured to operatively couple to the stator.

FIG. 11 illustrates one embodiment of a sterile barrier 400 that includes a stator 402. The sterile barrier 400 also includes a cap 404 configured as a protective cover for the stator 402. The stator 402 includes a plurality of coils 406 and is part of a two-phase, eight-pole stepper or brushless motor, as also shown in FIG. 12. The stator 402 also includes a plurality of contacts 408, which are rigid contacts in this illustrated embodiment, configured to mate with a plurality of contacts 410, which are also rigid, of a surgical robot's tool driver 412, which is also illustrated in FIG. 13.

The cap 404 can have a variety of configurations. As in this illustrated embodiment, the cap 404 can be plastic, such as a liquid crystal polymer, Teflon™ and glass fill (Vectra® A435), or other plastic. A distal portion 404*d* of the cap 404 can be thinner material than a proximal base 404*b* of the cap 404, which may facilitate transmission of the magnetic field through the distal portion 404*d* of the cap 404. For example, the distal portion 404*d* of the cap 404 can have a thickness in a range of about 0.005 to 0.007 in. A person skilled in the art will appreciate that a value may not be precisely at that value but nevertheless be considered to be about that value due to any number of factors, such as manufacturing tolerance and sensitivity of measurement equipment. The cap 404 can have a tolerance stack up fit, for example, in a range of about 0.001 to 0.002 in. to prevent interference.

The tool includes five motors in this illustrated embodiment, each associated with its own plurality of contacts 410, which are spring contacts in this illustrated embodiment, configured to mate with one of a plurality of stators 402 of the sterile barrier 400. The sterile barrier 400 in this illustrated embodiment thus has five stators 402. The tool driver 412 includes a transmitter 414, which is wireless in this illustrated embodiment, that is configured to transmit power to a surgical tool releasably coupled to the tool driver 412. The transmitter 414 can be configured to transmit a current that is in a range of, for example, about 50 to 400 mA across an air gap, such as with a LTC4120 wireless power transfer element. The transmitter 414 is a coil in this illustrated embodiment, e.g., a coil having dimensions of about 3 mm by 3 mm by 0.75 mm tall. The tool driver 412 also includes an antenna 416, which in this illustrated embodiment is a 3-D wireless antenna, that is configured to facilitate data transmission to/from the tool driver 412. In other embodiments, instead of the transmitter 414 configured to align with a corresponding transmitter of the surgical tool and the antenna 416 configured to align with a corresponding antenna of the surgical tool, the tool driver 412 can include an array of coils in a pattern (e.g., a linear pattern or a triangular pattern) configured to interface with at least one coil on the surgical tool. In such a case, the tool driver 412 can be configured to sense which of the coils in the array is most aligned with the at least one coil of the surgical tool and use the most aligned coil for communication.

Figure 14:
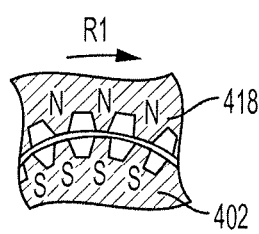
FIG. 14 is a partial schematic view of the coupled rotor and stator of FIG. 11.

FIGS. 11 and 12 also illustrate an embodiment of a rotor 418 of a surgical tool 420 configured to releasably couple to the tool driver 412 with the sterile barrier 400 positioned therebetween. The rotor 418 includes a plurality of permanent magnets in this illustrated embodiment. The number of magnets in the rotor 418 can be the same as the number of poles of the stator 402, e.g., eight in this illustrated embodiment, or can have a different number, e.g., a number in a range of four to eight. The surgical tool in this illustrated embodiment includes five rotors 418, one for operative coupling with each one of the stators 402. The rotor 418 is operatively coupled to an activation feature, in the form of a gear 422, which is operatively coupled to the surgical tool's end effector. Torque at the rotor 418 induced by the magnetic field generated via the stator 402 can thus activate, e.g., rotate, the gear 422 to thereby cause desired movement of the end effector and/or elongate shaft of the surgical tool 420. FIG. 14 illustrates rotational movement (arrow R1) of the rotor/stator coupling and shows gear teeth of the stator 402 and the rotor 418. The gear teeth are machined into interface areas of the stator 402 and the rotor 418 and can have gaps in a range of, e.g., about 0.001 to 0.003 in.

In at least some embodiments, the sterile barrier 400 can include an alignment mechanism, such as a plurality of wear ribs, as discussed further below. In addition to the wear ribs on the sterile barrier 400, wear ribs can be at an interface between the rotor 418 and the stator 402 to allow for a substantially zero air gap therebetween as the ribs wear away over use to completely seat the rotor 418 and the stator 402 against one another. If the interface includes wear ribs, a spring bias between the rotor 418 and the stator 402 can be present along an axis of rotation of the rotor 418 and stator 402 to drive the rotor 418 fully down onto the stator 402 during rotation, e.g., during the first few rotations of the rotor 418 and stator 402 to result in full seating.

Figure 15:
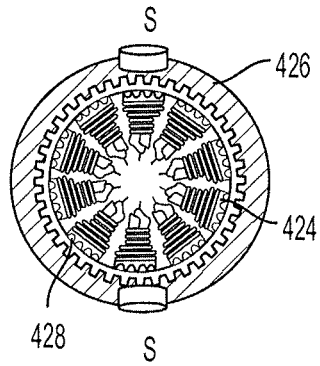
FIG. 15 is an end cross-sectional view of another embodiment of a rotor of a surgical tool coupled with a sterile barrier including a stator.
Figure 16:
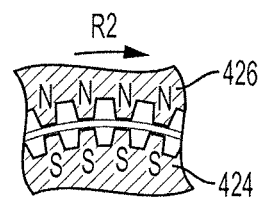
FIG. 16 is a partial schematic view of the coupled rotor and stator of FIG. 15.

FIG. 15 illustrates another embodiment of a stator 424 of a sterile barrier and a rotor 426 of a surgical tool. The stator 424 and the rotor 426 are configured and used similar to the stator 402 and the rotor 418, respectively, of FIG. 11, except that the stator 424 is part of a five-phase, ten-pole stepper or brushless motor. The sterile barrier includes a cap 428 that is configured and used similar to the cap 404 of FIG. 11. FIG. 16 illustrates rotational movement (arrow R2) of the rotor/stator coupling and shows gear teeth of the stator 424 and the rotor 426. The number of magnets in the rotor 426 can be the same as the number of poles of the stator 424, e.g., ten in this illustrated embodiment, or can have a different number, e.g., a number in a range of two to ten.

Figure 17:
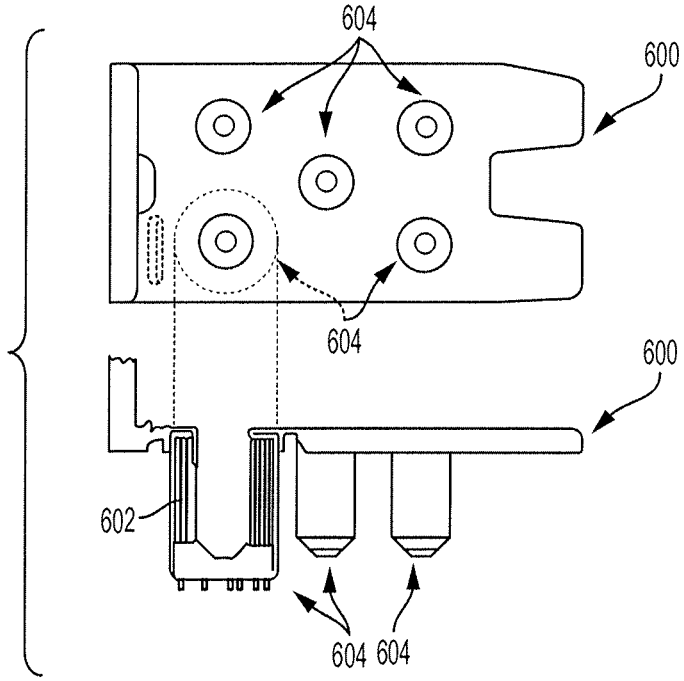
FIG. 17 is a top schematic view and a side schematic view of another embodiment of a sterile barrier that includes a stator.
Figure 18:
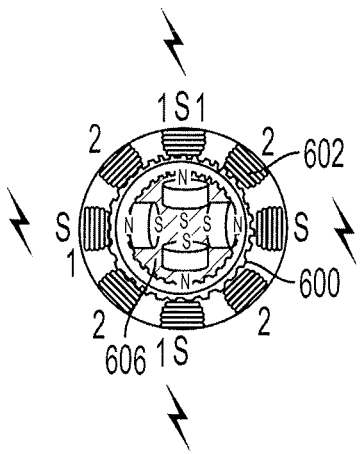
FIG. 18 is an end cross-sectional view of the sterile barrier of FIG. 17 coupled to a rotor.
Figure 19:
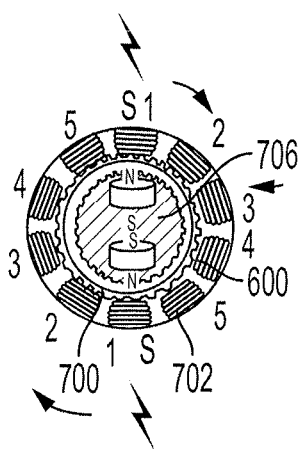
FIG. 19 is an end cross-sectional view of another embodiment of a sterile barrier coupled to a rotor.
Figure 20:
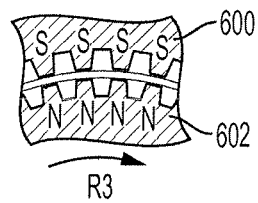
FIG. 20 is a partial schematic view of the coupled rotor and stator of FIG. 18.
Figure 21:
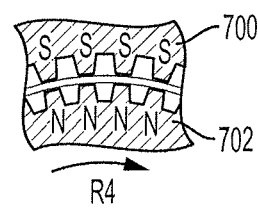
FIG. 21 is a partial schematic view of the coupled rotor and stator of FIG. 19.

FIGS. 17 and 18 illustrate another embodiment of a sterile barrier 600 that includes a stator 602. For clarity of illustration, only one set of stator coils 602 is shown on one of the sterile barrier's couplings 604 configured to couple to a surgical tool and a surgical robot on opposed sides thereof. Stator coils would also be attached to the sterile barrier's other four couplings 604. The stator coils 602 are attached in this illustrated embodiment by being molded therearound. The stator 602 is part of a two-phase, eight-pole stepper or brushless motor, although it may vary. For example, FIG. 19 illustrates a stator 702 of a sterile barrier 700 that is configured and used similar to the sterile barrier 600 of FIG. 17 except that the stator 702 is part of a five-phase, ten-pole stepper or brushless motor. FIG. 20 illustrates rotational movement (arrow R3) of the rotor/stator coupling of FIGS. 17 and 18 and shows gear teeth of the stator 602 and a rotor 606 of a surgical tool configured to be releasably coupled to the sterile barrier 600. FIG. 21 illustrates rotational movement (arrow R4) of the rotor/stator coupling of FIG. 19 and shows gear teeth of the stator 702 and a rotor 706 of a surgical tool configured to be releasably coupled to the sterile barrier 700. The rotors 606, 706 can each be a single core rotor. The single core rotor can have ferrous elements attached to either pole and can have a hybrid gearing machined into its north and south poles with an offset tooth pattern configured to allow both poles to attract and repel the same stator coil simultaneously.

Figure 22:
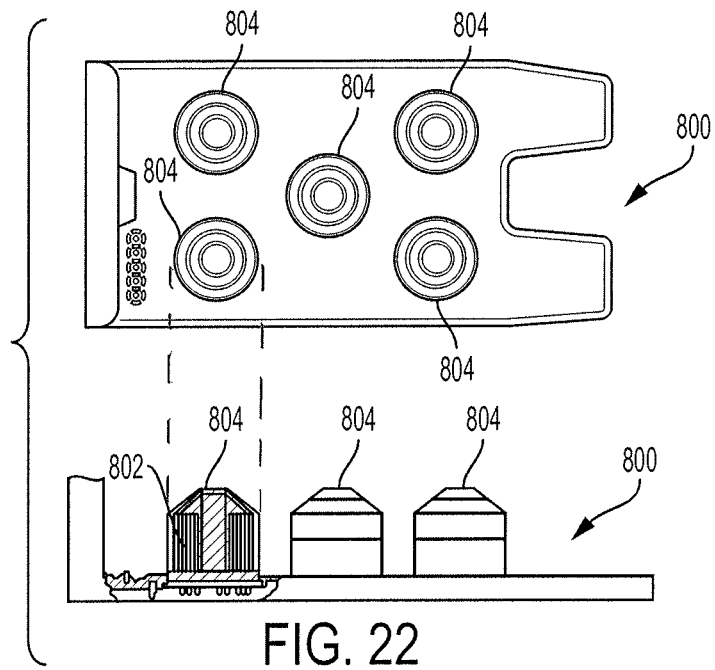
FIG. 22 is a top schematic view and a side schematic view of yet another embodiment of a sterile barrier that includes a stator.

FIG. 22 illustrates another embodiment of a sterile barrier 800 that includes a stator 802. The sterile barrier 800 is configured and used similar to the sterile barrier 600 of FIG. 17 except that while the sterile barrier 600 of FIG. 17 has an "inward" configuration, the sterile barrier 800 of FIG. 22 has an "outward" configuration. For clarity of illustration, only one set of stator coils 802 is shown on one of the sterile barrier's couplings 804 to tool driver. Stator coils are also be attached to the sterile barrier's other four couplings 804. The stator coils 802 are attached in this illustrated embodiment by being molded into the sterile barrier 800, e.g., into the couplings 804.

Instead of a stator being built entirely into a sterile barrier, a portion of the stator can be part of the sterile barrier, such as an array of ferrous plates being integrated into a circumferential track defined by a cylindrical outer surface between the releasably coupled stator and rotor. The ferrous plates can be aligned with metal plates of the stator and can allow contact between the stator poles and the plates on the non-sterile side of the sterile barrier. The ferrous plates can thus be configured as an extension of the stator integrated with the sterile barrier and thereby remove the need to throw away a whole stator with a disposable sterile barrier after its use. Instead, only the plates that are part of the sterile barrier need be discarded (as part of the disposable sterile barrier).

Figure 23:
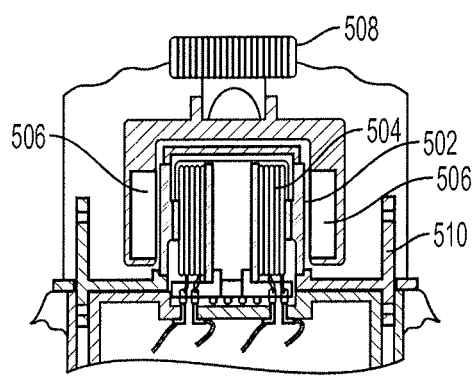
FIG. 23 is a side cross-sectional view of another embodiment of a sterile barrier coupled to a rotor.
Figure 24:
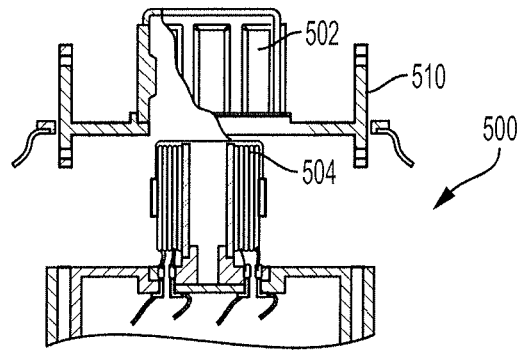
FIG. 24 is an exploded cross-sectional view of the sterile barrier of FIG. 23.
Figure 25:
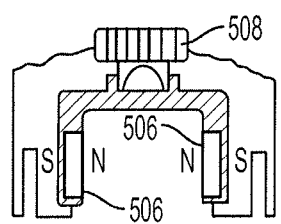
FIG. 25 is a side cross-sectional view of the rotor of FIG. 23.

FIGS. 23 and 24 illustrate another embodiment of a sterile barrier 500 that includes a stator. The sterile barrier 500 in this illustrated embodiment does not include a cap or contacts like the sterile barrier 400 of FIG. 11. The sterile barrier 500 in this illustrated embodiment includes a track 510 with a plurality of metal plates 502, eight in this illustrated embodiment, that are configured to become magnetic in response to a magnetic field generated by coils 504, eight in this illustrated embodiment. The metal plates 502 are arranged radially around a perimeter of the sterile barrier 500. A surgical tool configured to releasably couple to the sterile barrier 500 includes a rotor 506, as shown in FIGS. 24 and 25, in the form of a plurality of permanent magnets that are arranged radially around a perimeter of the tool. The rotor 506 is operatively coupled to an activation feature, in the form of a gear 508, which is operatively coupled to the surgical tool's end effector similar to that discussed above regarding the gear 422 of FIG. 11. The rotor 508 can have a hybrid gearing machined into its north (N) and south (S) poles with an offset tooth pattern configured to allow both poles to attract and repel the same stator coil simultaneously. The surgical tool includes five rotors 506, one for operatively coupling with each of the five stators of the sterile barrier 500.

Figure 26:
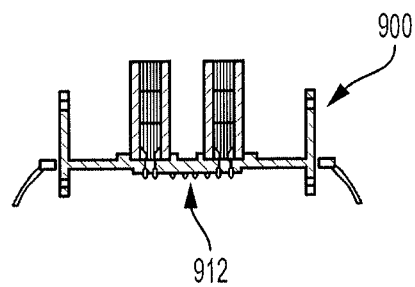
FIG. 26 is a side cross-sectional view of another embodiment of a sterile barrier that includes a stator.
Figure 27:
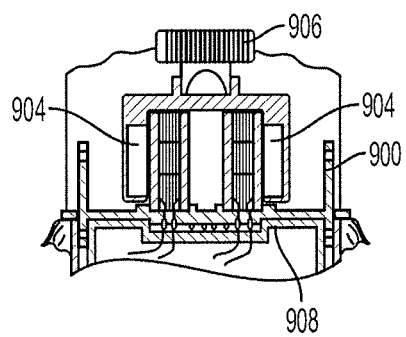
FIG. 27 is a side cross-sectional view of the sterile barrier of FIG. 26 coupled to a rotor and to a tool driver.
Figure 28:
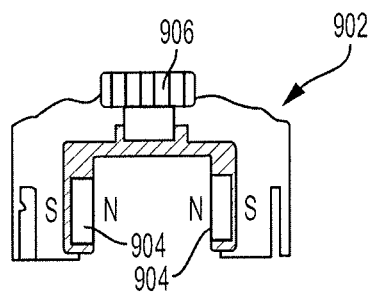
FIG. 28 is a side cross-sectional view of the rotor of FIG. 27.
Figure 29:
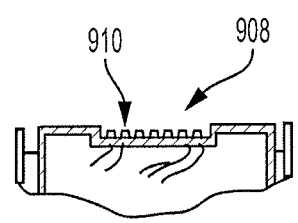
FIG. 29 is a side cross-sectional view of the tool driver of FIG. 27.

FIGS. 26 and 27 illustrate another embodiment of a sterile barrier 900 that includes a stator. The sterile barrier 900 in this illustrated embodiment is similar to the sterile barrier 500 of FIGS. 23 and 24 except that a track with plates is not provided between the releasably coupling of the sterile barrier 900 and a surgical tool 902, which is also shown in FIG. 28, that includes a rotor 904 configured to operably couple to the stator similar to the rotor 506 of FIGS. 24 and 25. The rotor 904 is operatively coupled to an activation feature, in the form of a gear 906, which is operatively coupled to the surgical tool's end effector similar to that discussed above regarding the gear 422 of FIG. 11. The sterile barrier 900 is also configured to couple to a tool driver 908 of a surgical robot, as shown in FIGS. 27 and 29, that has contacts 910 configured to couple to contacts 912 of the sterile barrier 900, similar to the contacts discussed above.

Figure 30:
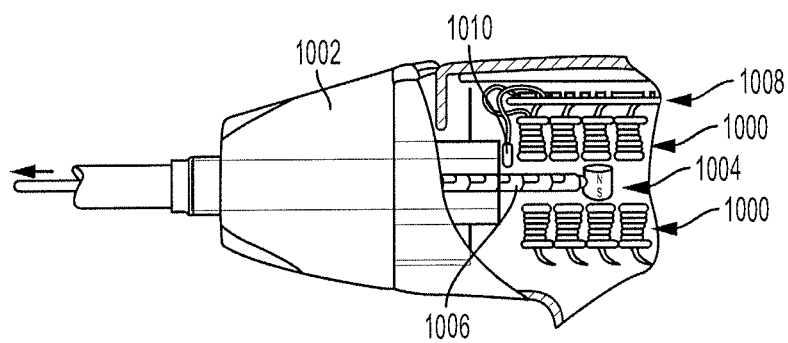
FIG. 30 is a side, partial cut-away view of an intermediate portion of a surgical device including a stator releasably coupled to a rotor.
Figure 31:
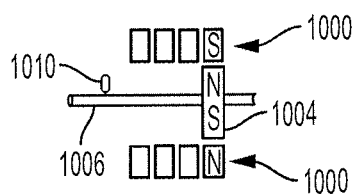
FIG. 31 is a schematic view of magnetic attraction of the stator and rotor of FIG. 30.
Figure 32:
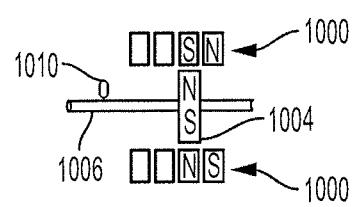
FIG. 32 is a schematic view of magnetic repelling of the stator and rotor of FIG. 30.

In some embodiments, a stator can be a set of electromagnets with a central single rotor. FIG. 30 illustrates one embodiment of such a stator 1000 for a surgical device 1002 with a linear motor. The stator 1000 includes a plurality of electromagnetic coils arranged around a single rotor 1004, which is in the form of a permanent magnet. FIG. 31 illustrates attraction of the rotor 1004 to the stator 1000, and FIG. 32 illustrates repulsion of the rotor 1004 from the stator 1000. The rotor 1004 is coupled to an activation feature 1006 operatively coupled to the end effector, as discussed above. The rotor 1004 can have ferrous elements attached to either pole thereof or can have a hybrid gearing mechanism machine into the north and south pole mechanisms with an offset tooth pattern to allow both poles to attract and repel the same stator coil simultaneously.

The device 1002 includes a circuit board 1008 that includes a controller configured to control the stator 1000, similar to that discussed above regarding the surgical robot's control of a stator. The device 1002 also includes a sensor 1010, e.g., an optical sensor, etc., configured to facilitate position control, similar to that discussed above.

The surgical device 1002 can be modular, with a proximal portion of the device 1002 that includes the stator 1000 being configured to releasably couple to a distal portion of the device 1002 that includes the rotor 1004, as discussed further below.

In at least some embodiments, a sterile barrier can be configured to mechanically align a tool driver, which includes one of a rotor and stator, and a surgical tool, which includes the other of the stator and rotor, that are coupled together with the sterile barrier therebetween. The sterile barrier can thus be configured to align the stator and rotor, which may facilitate efficient delivery of torque to the rotor and hence facilitate driving of the surgical tool's end effector and elongate shaft. The sterile barrier can include an alignment mechanism configured to cause the alignment of the stator and rotor. The alignment mechanism can be configured to automatically cause the alignment of the stator and rotor. The alignment mechanism can have a variety of configurations.

Figure 33:
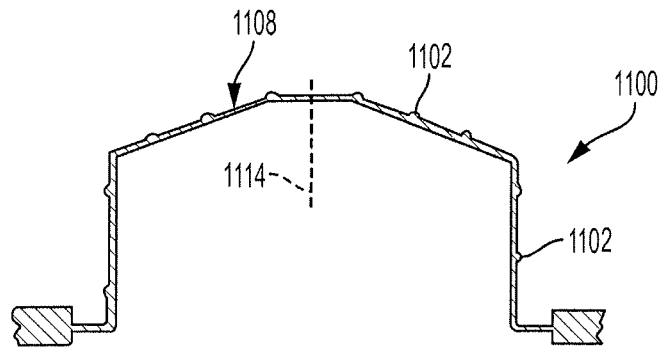
FIG. 33 is a side cross-sectional view of one embodiment of a sterile barrier including an alignment mechanism.
Figure 34:
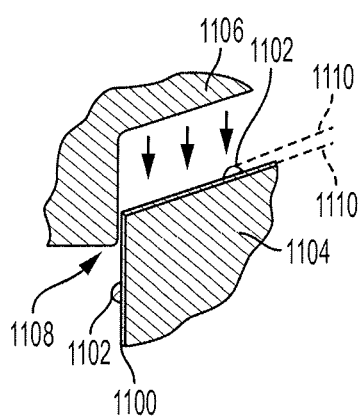
FIG. 34 is a side, cross-sectional, partial view of the sterile barrier of FIG. 33 coupled to a tool driver and being coupled to a surgical tool housing.
Figure 35:
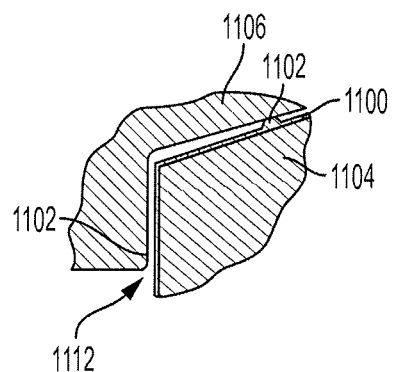
FIG. 35 is a side, cross-sectional, partial view of the sterile barrier of FIG. 34 coupled to the tool driver and surgical tool housing with the alignment mechanism partially worn away.

FIGS. 33-35 illustrate one embodiment of a sterile barrier 1100 that includes an alignment mechanism 1102 configured to align a tool driver 1104, which includes one of a rotor and stator, and a surgical tool 1106, which includes the other of the stator and rotor, that are coupled together with the sterile barrier 1000 therebetween. The alignment mechanism 1102 in this illustrated embodiment includes a plurality of wear ribs on a surface 1108 of the sterile barrier that faces the rotor, which in this illustrated embodiment is part of the surgical tool 1106. The stator is thus part of the tool driver 1104 in this illustrated embodiment and remains stationary while the rotor rotates. The surface 1108 is a conical face of the sterile barrier 1100 in this illustrated embodiment, as shown in FIG. 33.

The wear ribs in this illustrated embodiment extend circumferentially around the sterile barrier 1100 in a direction along which the rotor rotates relative to the stator. There are five wear ribs on the sterile barrier 1100, but there can any another number in other embodiments. The wear ribs can protrude outwardly from the surface 1108 at a distance 1110 in a range of, for example, about 0.001 to 0.002 in.

When the surgical tool 1106 is initially coupled to the tool driver 1104 with the sterile barrier 1100 therebetween, facing surfaces of the tool 1106 and driver 1104 will be separated by the distance 1110. When the rotor rotates relative to the stator, the surgical tool 1106, e.g., the surface thereof facing the driver 1104, will wear down the wear ribs, as shown in FIG. 35 in which the wear ribs have been worn down such that a small gap 1112, which is less than the distance 1110, exists between the surface 1108 and the surgical tool 1106. After further rotation of the rotor relative to the stator, the wear ribs will be worn away to allow for the air gap 1112 to be substantially eliminated (e.g., be substantially zero) such that the surface 1108 abuts the surgical tool 1106. A person skilled in the art will appreciate that the air gap may not be fully eliminated but nevertheless be considered to be substantially eliminated for any of a variety of reasons, such as manufacturing tolerances and sensitivity of measurement devices. The number of rotations of the rotor needed to wear away the wear ribs can vary based on, e.g., a material of the wear ribs, a material of the surgical tool that rubs against the wear ribs, and a speed of the rotor's rotation.

The wear ribs allow for automatic alignment of the surgical tool 1106 (e.g., the rotor thereof) and the tool driver 1104 (e.g., the stator thereof) by allowing the rotor and stator to naturally find a consistent centerline 1114 to rotate about.

In at least some embodiments, a sterile barrier located between a surgical tool and a surgical robot can include an electrical contact configured to facilitate electronic communication between the surgical tool and the surgical robot. The electrical contact can be an integral part of the sterile barrier. In this way, when the sterile barrier is coupled to a tool driver of the surgical robot and a housing of the surgical tool is removably and replaceably coupled to the tool driver, the electrical contact that is part of the sterile barrier between the tool driver and the housing will electrically connect the surgical tool and the surgical robot. The surgical tool and surgical robot may thus be directly electrically coupled, which may facilitate data transmission with little to no interference.

Figure 36:
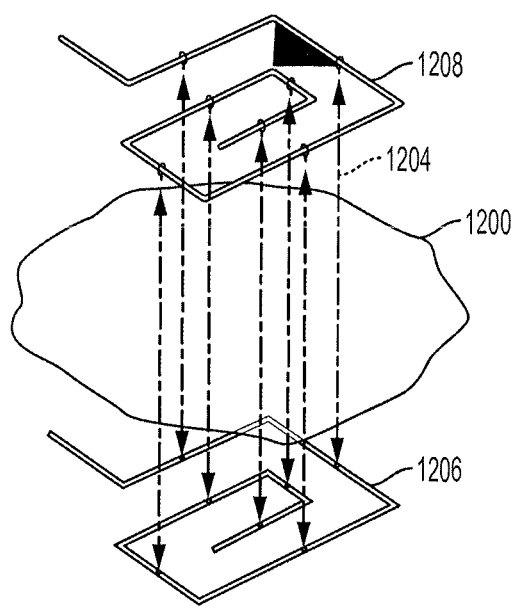
FIG. 36 is a side cross-sectional view of one embodiment of a sterile barrier including a plurality of electrical contacts.
Figure 37:
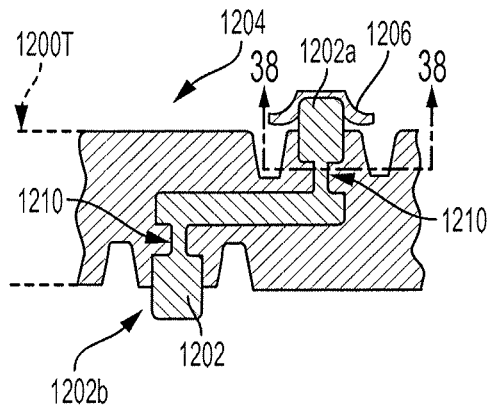
FIG. 37 is a side cross-sectional view of the sterile barrier and one of the electrical contacts.
Figure 38:
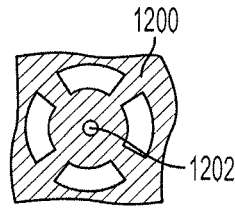
FIG. 38 is a cross-sectional view of a portion of the sterile barrier and the electrical contact of FIG. 37.
Figure 39:
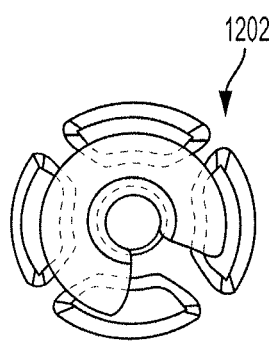
FIG. 39 is a top view of the electrical contact of FIG. 37.

FIG. 36 illustrates one embodiment of a sterile barrier 1200 including an electrical contact configured to facilitate electronic communication between a surgical tool and a surgical robot. The sterile barrier 1200 includes a plurality of electrical contacts 1202 (see FIGS. 37-39) at various locations 1204. FIG. 37 illustrates one of the electrical contacts 1202 with the sterile barrier 1200 coupled to a tool driver such that an antenna 1206 of the tool driver is in electrical contact with the electrical contacts 1202 at each of the locations 1204. The surgical tool also includes an antenna 1208 that similarly electrically contacts the electrical contacts 1202 at each of the locations 1204 when the surgical tool is releasably coupled to the surgical robot. The antennas 1206, 1208 are configured and used similar to the antenna 416 of FIG. 13 discussed above. The sterile barrier includes seven electrical contacts 1202 in this illustrated embodiment but can include another number of electrical contacts in other embodiments. Two antennas 1206, 1208 are shown in this illustrated embodiments, but other embodiments can include another number of antennas.

The electrical contacts 1202 can be configured as alignment mechanisms that provide mechanical alignment of the tool driver and surgical tool. The contacts 1202 can be configured to settle against the antenna 1206, 1208 so as to align the tool driver and surgical tool.

Each of the electrical contacts 1202 extends through a thickness 1200T of the sterile barrier 1200 along a tortuous path, as shown in FIG. 37. In this way, an end 1202a of the contact 1202 that couples to the surgical robot's antenna 1206 is laterally offset from an end 1202b of the contact 1202 that coupled to the surgical tool's antenna 1208. The lateral offset of ends 1202a, 1202b and tortuous path of the electrical contacts 1202 may help provide structural stability to the sterile barrier 1200 and/or may help prevent fluid, films, bacteria, and other matter from passing through the sterile barrier 1200, e.g., from the sterile side of the barrier 1200 to the non-sterile side of the barrier 1200 or vice versa.

The sterile barrier 1200 can be overmolded or injection molded on the electrical contacts 1202. The electrical contacts 1202 having variable diameters along their lengths, as shown in FIG. 37, may provide for overmolded tight zones 1210, e.g., areas of higher compression, to help secure the electrical contacts 1202 in the material of the sterile barrier 1200, which may be a plastic as mentioned above.

The sterile barrier 1200 can include one or more areas that are transparent or are semi-transparent to facilitate transmission of optical signals therethrough for communication purposes. For example, the sterile barrier 1200 can include a transparent area or semi-transparent area at each of the locations 1204 or can include a single transparent area or semi-transparent area that covers each of the locations 1204.

As an alternative to the electrical contacts, a plastic sterile barrier can instead include metallic or other electrically doped plastic elements therein. The doped elements can be ultrasonically or thermally fused to the plastic sterile barrier, thereby allowing the doped elements to conduct electrically while the sterile barrier serves to prevent fluid, films, bacteria, and other matter from passing therethrough. The doped elements can be configured to receive positive sharp pins from each of the surgical tool (e.g., the tool housing thereof) and the surgical robot (e.g., the tool driver thereof) to create an electrical bridge between the surgical tool and the surgical robot, or they could be a conductor with spring clips applied to both the surgical tool and the surgical robot.

Figure 40:
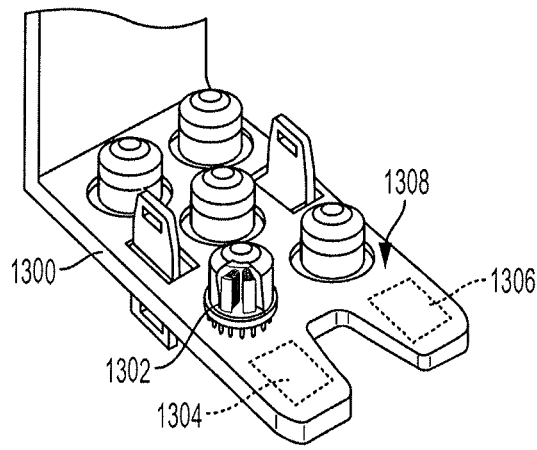
FIG. 40 is a perspective view of another embodiment of a sterile barrier that includes a magnetic shield.

FIG. 40 illustrates one embodiment of a sterile barrier 1300 that has a stator 1302 included therewith (for clarity of illustration only one of the stators is shown at the five locations where stators are located), that has a thinned region 1304 at a location where the sterile barrier 1300 couples to a transmitter of a surgical robot's tool driver (e.g., the transmitter 414 of FIG. 13), and that has a thinned region 1306 at a location where the sterile barrier 1300 couples to an antenna of the tool driver (e.g., the antenna 416 of FIG. 13). The thinned regions 1304, 1306 on the sterile barrier's surface 1308 that faces the tool driver have a smaller thickness than a remainder of the surface 1308. The thinner material in these regions 1304, 1306 may facilitate wireless transmission of signals therethrough.

In at least some embodiments, a shield can be located between a rotor and a stator on opposite sides of a sterile barrier. The shield can be configured to help isolate a magnetic field that extends between the rotor and stator and across the sterile barrier. In at least some embodiments, the sterile barrier can include the shield configured to provide a magnetic shield for a magnetic field that extends across the sterile barrier between the rotor and stator, e.g., between a surgical tool and surgical robot where one of the tool and robot include the rotor and the other includes the stator.

Figure 41:
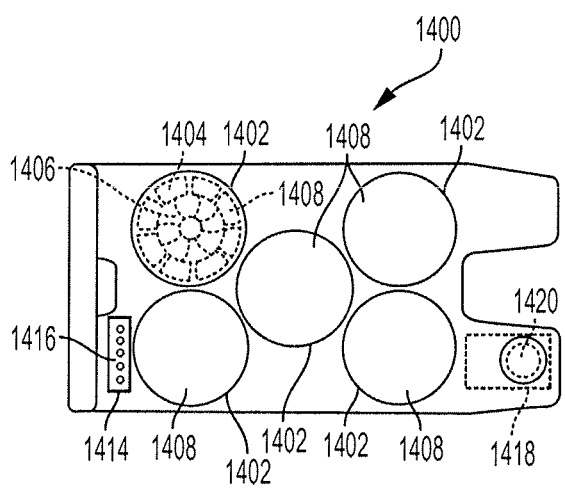
FIG. 41 is a top view of the sterile barrier of FIG. 40.
Figure 42:
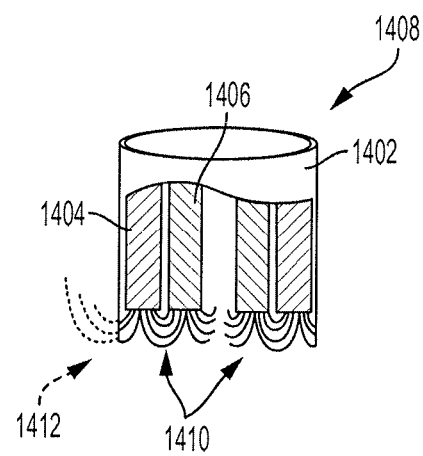
FIG. 42 is a side, partial cut-away view of a portion of the sterile barrier of FIG. 40 coupled to a rotor and generating a magnetic field.

FIG. 41 illustrates one embodiment of a sterile barrier 1400 that includes a shield 1402 configured to provide a magnetic shield for a rotor and stator located on opposite sides of the sterile barrier 1400. The sterile barrier 1400 is configured for use with a tool driver with five motors and hence has five shields 1402, one for each of the five stator/rotor assemblies. For clarity of illustration, FIGS. 41 and 42 only show one of the stator/rotor assemblies, which includes a rotor 1404 and a stator 1406. The shield 1402 in this illustrated embodiment includes woven mu-metal wrapped around each of the sterile barrier's couplings 1408 that have the stator/rotor assemblies therein. The shield 1402 is thus configured to radially contain a magnetic field. FIG. 42 shows a magnetic field 1410 between the rotor 1404 and stator 1406 that is shielded by the shield 1402 so as to not extend radially outside the coupling 1408. By way of contrast, FIG. 42 also shows a magnetic field 1412 that would exist were the shield 1402 absent. The magnetic field 1412 extends radially outside the coupling 1408, where it could interfere with other electrical components. The sterile barrier 1400 in this illustrated embodiment also includes a shield 1414 for data/control contacts 1416 and a shield 1418 for a power coil 1420. The shields 1414, 1418 in this illustrated embodiment are also woven mu-metal.

The sterile barrier 1400 of FIG. 41 includes multiple shields 1402 for the plurality of rotor/stator assemblies, with each of the shields 1402 being independent from one another. In other embodiments, a sterile barrier can include a single shield for a plurality of rotor/stator assemblies. A single shield may be easier to manufacture and/or have lower cost than a plurality of shields. The single shield can be electrically connected and connected to ground of a tool driver coupled to the sterile barrier, which may allow the shield to also serve as a radiofrequency or other energized particle/wave shield.

Figure 43:
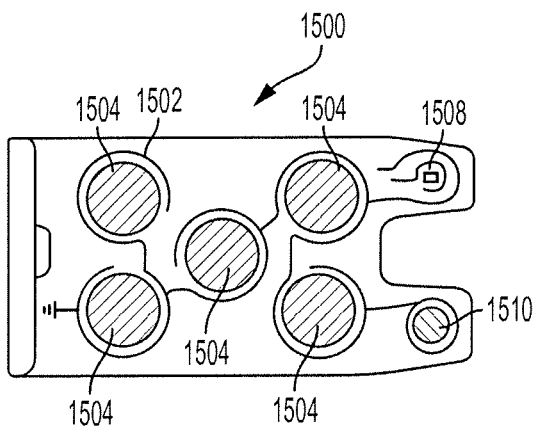
FIG. 43 is a top view of yet another embodiment of a sterile barrier that includes a magnetic shield.
Figure 44:
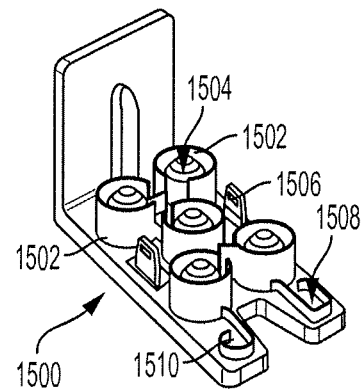
FIG. 44 is a perspective view of the sterile barrier of FIG. 43.

FIGS. 43 and 44 illustrate one embodiment of a sterile barrier 1500 that includes a single shield 1502 configured to provide a magnetic shield for a rotor and stator located on opposite sides of the sterile barrier 1500. The shield 1502 in this illustrated embodiment includes woven mu-metal wrapped around a partial circumference of each of the sterile barrier's couplings that have the stator/rotor assemblies 1504 therein. The shield 1502 is thus configured to provide radial protection for the magnetic fields generated at the stator/rotor assemblies 1504. The shield 1502 in this illustrated embodiment also wraps partially around each of an antenna 1508 and a power coil 1510 and is thus configured to provide a magnetic shield for more than one magnetic source simultaneously, e.g., for each of the rotor/stator assemblies 1504, for the antenna 1508, and for the power coil 1510. Connecting portions 1506 of the shield 1502 extend between adjacent ones of the couplings, antenna 1508, and power coil 1510. A height of the shield 1502 can be less in the connecting portions 1506 than around the couplings, antenna 1508, and power coil 1510 where the shield can extend a full height thereof as shown in FIG. 44 (and in FIG. 42 for the shield 1402).

Figure 45:
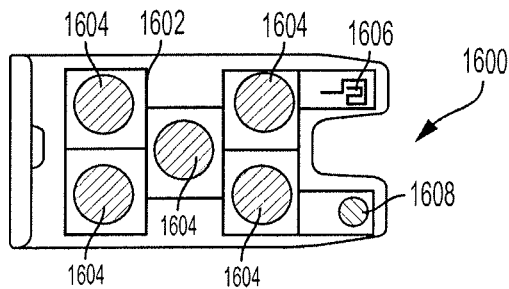
FIG. 45 is a top view of still another embodiment of a sterile barrier that includes a magnetic shield.

FIG. 45 illustrates another embodiment of a sterile barrier 1600 that includes a single shield 1602 configured to provide a magnetic shield for a rotor and stator located on opposite sides of the sterile barrier 1600. In this illustrated embodiment, the shield 1600, e.g., woven mu-metal material, extends fully around each of the sterile barrier's couplings and stator/rotor assemblies 1604 therein, and the shield 1600 extends around each of an antenna 1606 and a power coil 1608.

In at least some embodiments, a shield located between a rotor and a stator on opposite sides of a sterile barrier can be a multi-part shield where a surgical tool on one side of the sterile barrier includes a first part of the shield and a surgical robot on the other side of the sterile barrier includes a second part of the shield. The multi-part shield can be configured to connect together when the surgical tool is releasably coupled to the surgical robot with the sterile barrier therebetween.

Figure 46:
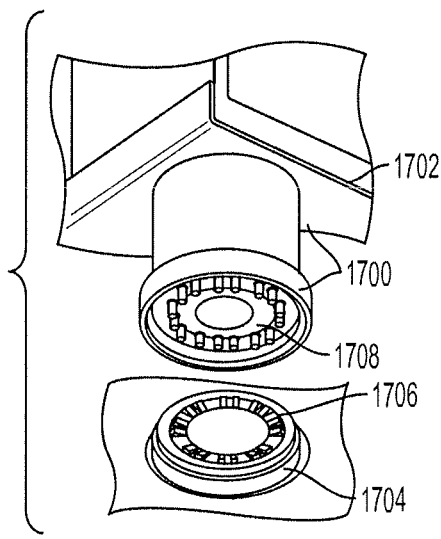
FIG. 46 is a perspective partial view of a multi-part magnetic shield that is unassembled.
Figure 47:
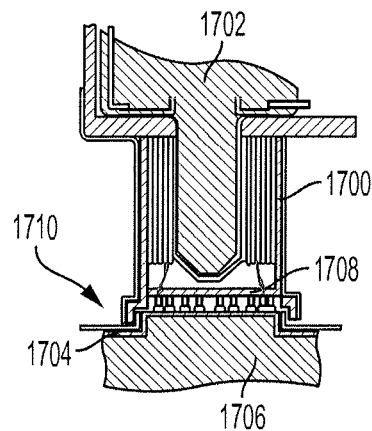
FIG. 47 is a side cross-sectional partial view of the magnetic shield of FIG. 46 assembled.

FIGS. 46 and 47 illustrate one embodiment of a multi-part shield that includes a first shield part 1700 on a surgical tool 1702 (e.g., on a housing thereof) and a second shield part 1704 on a surgical robot 1706 (e.g., on a tool driver thereof). The surgical tool 1702 is configured to releasably couple to the surgical robot 1706 with a sterile barrier 1708 therebetween. The first and second shield parts 1700, 1704 in this illustrated embodiment are each woven mu-metal that are wrapped around their respective rotor and stator. As shown in FIG. 47, the first and second shield parts 1700, 1704 overlap at an interface region 1710 where the tool 1702 releasably couples to the surgical robot 1706. The first and second shield parts 1700, 1704 may thus provide a full magnetic shield when the tool 1702 and surgical robot 1704 are assembled together in releasable attachment. In at least some embodiments, the sterile barrier 1708 can include a third shield part configured to assemble with the first and second shield parts 1700, 1704 to provide further magnetic shield protection.

As mentioned above, in some embodiments, a sterile barrier can be positioned between a proximal portion of a surgical tool and a distal portion of the surgical tool that is releasably coupled to the surgical tool's proximal portion. The surgical tool can thus be modular, with different distal portions able to be selectively attached to the proximal portion. The tool's proximal portion can include one of a stator and a rotor, and the tool's distal portion can include the other of the stator of the rotor. When the distal portion is removably and replaceably coupled to the proximal portion with the sterile barrier therebetween, an electromagnetic field can extend across the sterile barrier between the rotor and stator, similar to that discussed above, and thereby cause movement of the tool's elongate shaft (e.g., rotation thereof relative to the tool's proximal portion) and/or the tool's end effector (e.g., articulation of the end effector relative to the elongate shaft, opening of jaws of the end effector, closing of jaws of the end effector, or rotation of the end effector in tandem with rotation of the elongate shaft).

FIG. 48 illustrates one embodiment of a surgical tool 1800 including a proximal portion 1802 configured to releasably couple to a distal portion 1804 to form the tool 1800. FIG. 49 shows a cross-section of a portion of the tool 1800 where the proximal and distal portions 1802, 1804 are connected.

The proximal portion 1802, which is also shown in FIG. 50, can have a variety of configurations. As in this illustrated embodiment, the proximal portion 1802 can include a handle 1806, a sterile barrier 1808, and a stator housing unit 1810 that houses a stator. The handle 1806 is configured to be handheld by a user and manipulated to control movement of the surgical tool's elongate shaft 1812 and end effector (not shown), such as by pressing a trigger button 1814 or control buttons 1816, 1818. The trigger button 1814 and control buttons 1816, 1818 are operatively connected to a circuit board (not shown) disposed in the handle 1806 that includes a controller configured to control the stator 1810, similar to that discussed above regarding the surgical robot's control of a stator. The handle 1806 can include the buttons 1814, 1816, 1818 and/or other actuation mechanisms, such as control buttons on an opposite side of the handle 1806 (obscured in FIG. 48), a rotating knob, a movable trigger, switches, etc. The handle 1806 also has disposed therein a power source (e.g., at least one battery) configured to provide power to components therein.

The sterile barrier 1808 in this illustrated embodiment is a clamshell configured to releasably seat on the handle 1806. The releasability of the sterile barrier 1808 may facilitate cleaning of the tool 1800 and/or the sterile barrier 1808. The sterile barrier 1808 can be configured to be handheld with the handle 1806. The sterile barrier 1808 is configured to provide an interface on which one side (distal side) including the tool's distal portion 1804 and the stator unit 1810 is sterile and on which the other side (proximal side) including the handle 1806 is not sterile.

Various embodiments of buttons, power sources, actuation of handheld surgical tools, and sterile barriers for handheld surgical tools are further described in Intl. Pat. Pub. No. WO 2016/057225 entitled "Handheld Electromechanical Surgical System" filed Sep. 24, 2015, which is hereby incorporated by reference in its entirety.

Figure 51:
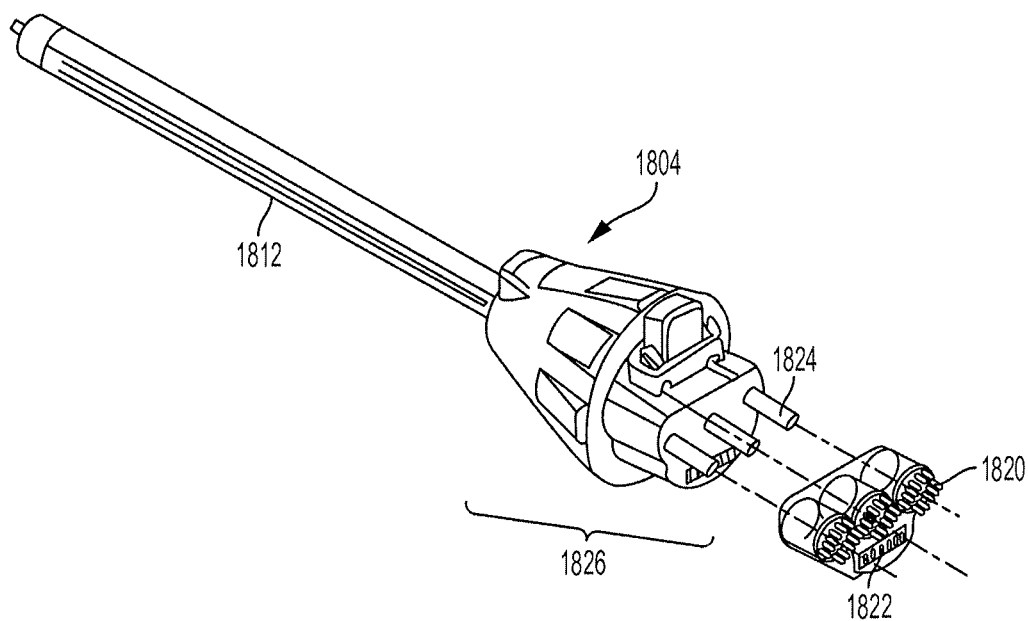
FIG. 51 is a perspective view of the distal portion and a stator of the proximal portion of the surgical device of FIG. 48.

The stator includes a plurality of coils 1820. The tool 1800 includes three coils 1820 in this illustrated embodiment but can include another number of coils in other embodiments. The coils 1820 can be distal-facing, as shown in FIGS. 48, 50, and 51, which may facilitate their releasable coupling with a rotor 1824 of the tool's distal portion 1804. The stator unit 1810 that has houses the stator can include a circuit board interface 1822 configured to electrically connect with the tool's circuit board to facilitate control of the stator.

The tool's distal portion 1804 includes an elongate shaft 1812 that extends distally from the handle 1806 when the distal portion 1804 is releasably coupled to the proximal portion 1802. An end effector (not shown) is at a distal end of the shaft 1812. The end effector can be fixedly attached to the shaft 1812 or can be removably and replaceably coupled thereto. A distal region of the distal portion 1804 defines a nozzle area 1826 of the assembled tool 1800, as illustrated in FIG. 48. As mentioned above, the distal portion 1804 includes a rotor configured to releasably couple to the stator 1810. The rotor includes a plurality of rods 1824, three in this illustrated embodiment to correspond to the three coils 1820 of the stator. The rods 1824 are configured to be received in respective ones of the coils 1820, as shown in FIGS. 49 and 51. The distal portion 1804 also include an activation feature, in the form of a pair of planet gears 1828 (see FIG. 48), operatively coupled to the end effector and configured to be activated by the rotor. The moving parts to impart end effector movement (and also possible elongate shaft movement) can thus all be located distal to the sterile barrier 1808 since the moving rods 1824 of the rotor and the moving activation feature are located distal to the sterile barrier 1808.

In other embodiments, the proximal portion 1802 can include a rotor and the distal portion 1804 configured to releasably couple to the proximal portion 1802 can include a stator, similar to that discussed above regarding surgical tools and surgical robots that can each include one of a stator and a rotor.

Figure 52:
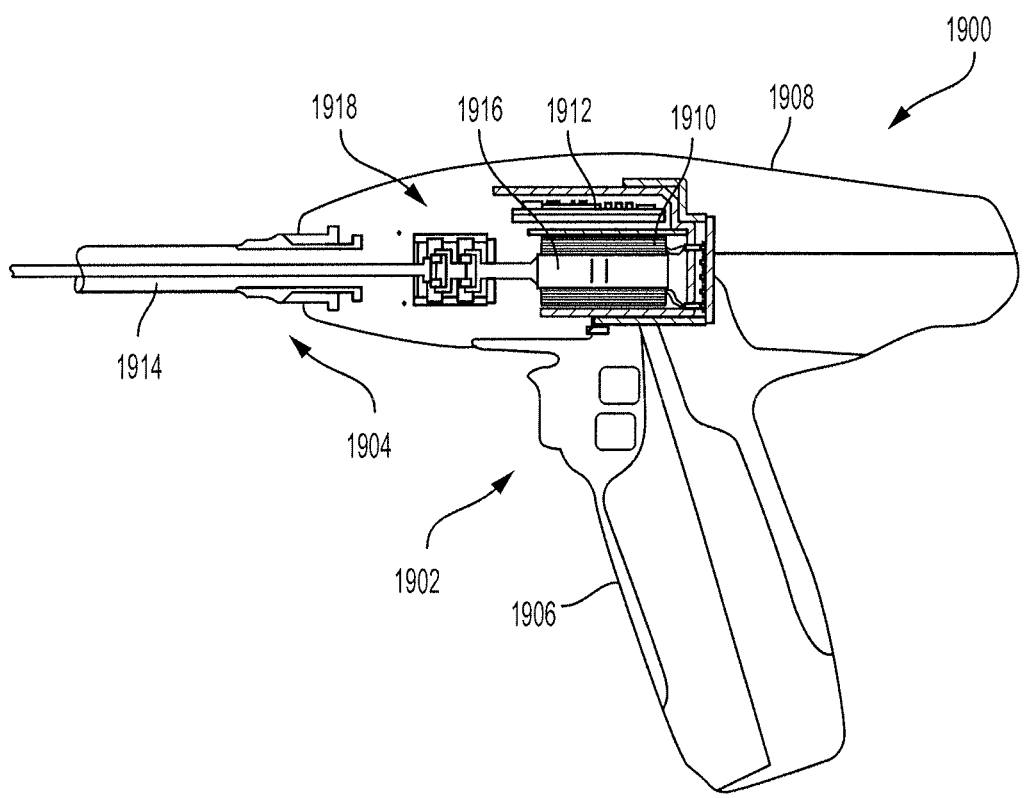
FIG. 52 is a side transparent view of another embodiment of a surgical device including a proximal portion and a distal portion that is releasably coupled to the proximal portion.

FIG. 52 illustrates another embodiment of a surgical tool 1900 including a proximal portion 1902 configured to releasably couple to a distal portion 1904 to form the tool 1900. The proximal portion 1902 is configured and used similar to the proximal portion 1802 of FIG. 48, e.g., includes a handle 1906, a sterile barrier 1908 in the form of a clamshell, a stator housing unit 1920 that houses a stator that includes a plurality of coils 1910, a circuit board 1912 operatively connected to the stator, and a power source (not shown). As shown in FIGS. 53 and 54, the stator housing unit 1920 includes contacts 1922 configured to operatively couple to the circuit board 1912 and includes contacts 1924 configured to operatively couple to a transmitter for data transmission. The distal portion 1904, which is also shown in FIG. 53, is configured and used similar to the distal portion 1804 of FIG. 48, e.g., includes an elongate shaft 1914 with an end effector (not shown) at a distal end thereof, a rotor including a plurality of rods 1916, and an activation feature 1918 in the form of two planet gears. In this illustrated embodiment, the rods 1916 are enclosed by walls 1926, which may protect the rods 1916 prior to coupling with the stator coils 1910, may protect the rods 1916 and the coils 1910 after the releasable coupling of the proximal and distal portions 1902, 1904, and/or may facilitate aligned insertion of the rods 1916 into the stator.

FIG. 55 illustrates another embodiment of a surgical tool 2000 including a proximal portion 2002 configured to releasably couple to a distal portion 2004 to form the tool 2000. The proximal portion 2002 is configured and used similar to the proximal portion 1802 of FIG. 48, e.g., includes a handle 2006, a sterile barrier (not shown), a stator housing unit 2008 that houses a stator that includes a plurality of coils 2010 (also shown in FIGS. 56-58), a circuit board 2012 (see FIGS. 56 and 57) operatively connected to the stator, and a power source (not shown). As shown in FIG. 56, the stator housing unit 2008 also includes contacts 2018 configured to operatively couple to the circuit board 2012 and includes contacts 2020 configured to operatively couple to a transmitter for data transmission The distal portion 2004 is configured and used similar to the distal portion 1804 of FIG. 48, e.g., includes an elongate shaft (not shown) with an end effector at a distal end thereof, a rotor including a plurality of rods 2014 (also shown in FIG. 58), and an activation feature (not shown). In this illustrated embodiment, an outermost two of the three rods 2014 are enclosed by walls 2016 similar to the walls 1926 of FIG. 53.

Figure 58:
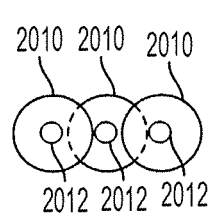
FIG. 58 is an end schematic view of the stator and rotor of FIG. 55 coupled together.

In this illustrated embodiment, the stator coils 2010 overlap in a lateral or horizontal (e.g., side to side) direction, as shown in FIGS. 56-58. The overlap of the coils 2010 allows the motor to occupy less space in the handle 2006 of the tool 2000, as compared to coils of the same diameter that do not overlap, and thus allow for a smaller device and/or allow more space for other components in the handle 2006. Also, the overlap of the coils 2010 allows larger coils to be used in the same amount of space that non-overlapping coils would occupy in the tool 2000. Larger coils may allow larger torques to be imparted to the rotor because more amp turns are possible, thereby creating larger magnetic field strengths. To allow for the overlap, the outermost two of the three coils 2010 (labeled B and C in FIGS. 56 and 57) are positioned distal to a center one of the three coils 2010 (labeled A in FIGS. 56 and 57). A center one of the rotor rods 2014 thus extends proximally farther than the outermost two of the rods 2014, as shown in FIG. 55, in order to extend far enough proximally to effectively couple to the center one of the stator coils 2010.

Figure 59:
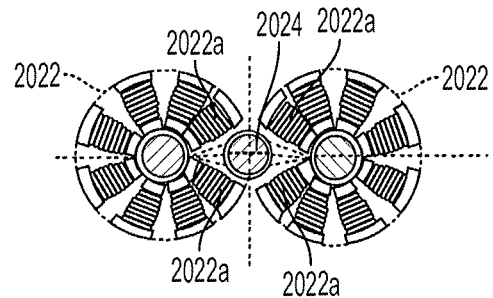
FIG. 59 is a schematic cross-sectional, partial view of another embodiment of a stator of a surgical device.

The center stator coil 2010 in this illustrated embodiment is offset entirely proximally beyond the two outer stator coils 2010, as shown in FIGS. 55 and 57. In other words, a distal end of the center stator coil 2010 is proximal to proximal ends of the outer stator coils 2010. Adjacent coils thus do not interfere with one another, e.g., stator coil A in FIGS. 56 and 57 does not interfere with either stator coil B or stator coil C. In other embodiments, the center stator coil 2010 may not be offset entirely proximally beyond the two outer stator coils 2010, e.g., the distal end of the center stator coil 2010 may be distal to the proximal ends of the outer stator coils 2010. The center stator coil 2010 may thus impinge laterally on space of the two outer stator coils 2010. To provide for better lateral spacing in such an arrangement, as shown in one embodiment in FIG. 59, outer stator coils 2022 spaced laterally outward on either side of a center stator coil (not shown) can have coils 2022a angled or bent outward. A rotor rod 2024 that operatively couples with the center stator coil may thus have enough space between the outer stator coils 2022 to extend proximally to the center stator coil for operative coupling therewith. The angled coils 2022a can have a different number or manner of wiring than the other coils in its associated stator to help all the coils achieve equal magnetic force, e.g., the two angled coils 2022a in the left-most stator (as seen in FIG. 59) can have a different number or manner of wiring than the other six coils in that stator.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 60:
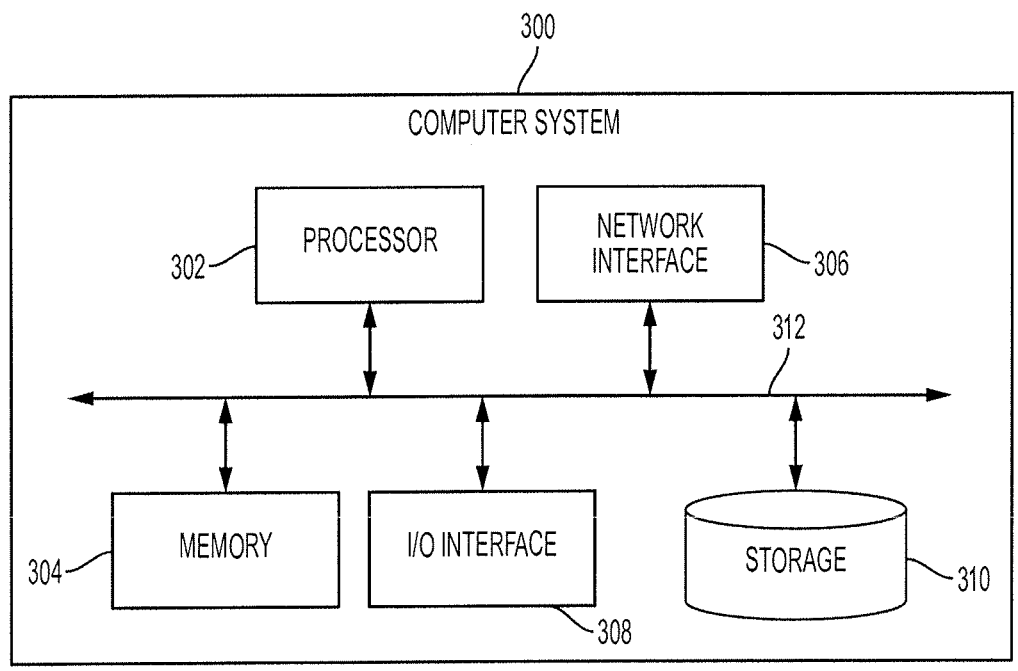
FIG. 60 is a schematic view of one embodiment of a computer system.

FIG. 60 illustrates one exemplary embodiment of a computer system 300. As shown, the computer system 300 includes one or more processors 302 which can control the operation of the computer system 300. "Processors" are also referred to herein as "controllers." The processor(s) 302 can include any type of microprocessor or central processing unit (CPU), including programmable general-purpose or special-purpose microprocessors and/or any one of a variety of proprietary or commercially available single or multi-processor systems. The computer system 300 can also include one or more memories 304, which can provide temporary storage for code to be executed by the processor(s) 302 or for data acquired from one or more users, storage devices, and/or databases. The memory 304 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 300 can be coupled to a bus system 312. The illustrated bus system 312 is an abstraction that represents any one or more separate physical busses, communication lines/interfaces, and/or multi-drop or point-to-point connections, connected by appropriate bridges, adapters, and/or controllers. The computer system 300 can also include one or more network interface(s) 306, one or more input/output (10) interface(s) 308, and one or more storage device(s) 310.

The network interface(s) 306 can enable the computer system 300 to communicate with remote devices, e.g., other computer systems, over a network, and can be, for non-limiting example, remote desktop connection interfaces, Ethernet adapters, and/or other local area network (LAN) adapters. The IO interface(s) 308 can include one or more interface components to connect the computer system 300 with other electronic equipment. For non-limiting example, the IO interface(s) 308 can include high speed data ports, such as universal serial bus (USB) ports, 1394 ports, Wi-Fi, Bluetooth, etc. Additionally, the computer system 300 can be accessible to a human user, and thus the IO interface(s) 308 can include displays, speakers, keyboards, pointing devices, and/or various other video, audio, or alphanumeric interfaces. The storage device(s) 310 can include any conventional medium for storing data in a non-volatile and/or non-transient manner. The storage device(s) 310 can thus hold data and/or instructions in a persistent state, i.e., the value(s) are retained despite interruption of power to the computer system 300. The storage device(s) 310 can include one or more hard disk drives, flash drives, USB drives, optical drives, various media cards, diskettes, compact discs, and/or any combination thereof and can be directly connected to the computer system 300 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 60 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 300 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 300 can also include a web server for generating and/or delivering the web pages to client computer systems.

In an exemplary embodiment, the computer system 300 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a proximal handle portion of a surgical tool including a stator;
   a distal portion of the surgical tool configured to removably and replaceably couple to the proximal handle portion, the distal portion including a rotor and including an end effector configured to be driven by a magnetic field extending between the rotor and the stator;
   a sterile barrier coupled to the proximal handle portion and configured to provide a sterile environment for the distal portion including the rotor when the distal portion is removably and replaceably coupled to the proximal handle portion; and a gear operatively coupled to the end effector and to the rotor;

wherein, in response to torque induced at the rotor by the magnetic field, the gear is configured to rotate and thereby drive the end effector.

2. The device of claim 1, wherein the distal portion is configured to removably and replaceably couple to the proximal portion by engaging the rotor with the stator.

3. The device of claim 1, wherein the sterile barrier is removably and replaceably coupled to the proximal handle portion.

4. The device of claim 1, wherein the stator is integrally coupled to the proximal handle portion.

5. The device of claim 1, wherein the stator is removably and replaceably coupled to the proximal handle portion.

6. The device of claim 1, wherein the magnetic field drives the end effector to move without the surgical tool being mechanically driven by the tool driver.

7. The device of claim 1, wherein the end effector is configured to be driven to effect at least one of closing the end effector, opening the end effector, articulating the end effector relative to an elongate shaft having the end effector at a distal end thereof, rotating the end effector relative to the elongate shaft, and rotating the end effector and the elongate shaft as a unit about a longitudinal axis of the elongate shaft.

8. A surgical device, comprising:
an elongate shaft having an end effector at a distal end thereof that is configured to engage tissue;
a proximal handle configured to be handheld and to removably and replaceably couple to the elongate shaft such that the elongate shaft extends distally from the proximal handle;
a sterile barrier coupled to the proximal handle and configured to provide a sterile environment distal thereof with a non-sterile environment being proximal thereto, the elongate shaft and the end effector being in the sterile environment when the proximal handle is removably and replaceably coupled to the elongate shaft; and
magnetic members configured to generate a magnetic field across the sterile barrier when the proximal handle is removably and replaceably coupled to the elongate shaft and thereby cause movement of the end effector.

9. The device of claim 8, wherein the magnetic members includes a rotor of the elongate shaft and a stator of the proximal handle.

10. The device of claim 9, wherein the rotor is at a proximal end of the elongate shaft, the stator is at a distal end of the proximal handle, and the proximal handle is configured to be removably and replaceably coupled to the elongate shaft by attaching the rotor to the stator.

11. The device of claim 8, wherein the proximal handle includes a power source configured to cause the generation of the magnetic field.

12. The device of claim 8, wherein the movement of the end effector includes at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

13. A surgical method, comprising:
coupling a distal portion of a handheld surgical device to a proximal portion of the handheld surgical device with a handle in the proximal portion being in a non-sterile environment and a sterile barrier of the handheld surgical device providing a sterile environment for the distal portion including an elongate shaft having an end effector at a distal end thereof; and
generating a magnetic field that extends between the proximal portion in the non-sterile environment and the distal portion in the sterile environment and thereby causing the end effector to move, wherein the magnetic field causes the movement of the end effector without the surgical tool being mechanically driven by the tool driver.

14. The method of claim 13, wherein coupling the distal portion to the proximal portion electrically couples a rotor of the distal portion to a stator of the proximal portion, and the magnetic field extends between the stator and the rotor.

15. The method of claim 13, further comprising, prior to coupling the distal portion to the proximal portion, coupling the sterile barrier to the proximal portion.

16. The method of claim 13, wherein the movement of the end effector includes at least one of closing the end effector, opening the end effector, articulating the end effector relative to the elongate shaft, rotating the end effector relative to the elongate shaft, and rotating the end effector and the elongate shaft as a unit about a longitudinal axis of the elongate shaft.

17. The method of claim 14, wherein the magnetic field induces torque at the rotor that causes the movement of the end effector.

18. The device of claim 9, further comprising a gear operatively coupled to the end effector and to the rotor;
wherein, in response to torque induced at the rotor by the magnetic field, the gear is configured to rotate and thereby drive the end effector.

* * * * *